(12) United States Patent
Valle et al.

(10) Patent No.: US 9,670,493 B2
(45) Date of Patent: Jun. 6, 2017

(54) LOW-PHOSPHATE REPRESSIBLE PROMOTER

(71) Applicant: Codexis, Inc., Redwood City, CA (US)

(72) Inventors: Fernando Valle, Burlingame, CA (US); Patricia Choudhary, Foster City, CA (US); Robert Osborne, Oakland, CA (US); Saul Nitsche Rocha, Redwood City, CA (US); Monica Bhatia, Sunnyvale, CA (US); U Loi Lao, Redwood City, CA (US); Yihui Zhu, Redwood City, CA (US)

(73) Assignee: Codexis, Inc., Redwood, CA (US)

( * ) Notice: Subject to any disclaimer, the term of this patent is extended or adjusted under 35 U.S.C. 154(b) by 59 days.

(21) Appl. No.: 14/773,554

(22) PCT Filed: Mar. 13, 2014

(86) PCT No.: PCT/US2014/025332
§ 371 (c)(1),
(2) Date: Sep. 8, 2015

(87) PCT Pub. No.: WO2014/159850
PCT Pub. Date: Oct. 2, 2014

(65) Prior Publication Data
US 2016/0017342 A1 Jan. 21, 2016

Related U.S. Application Data

(60) Provisional application No. 61/783,641, filed on Mar. 14, 2013.

(51) Int. Cl.
| | |
|---|---|
| C07H 21/04 | (2006.01) |
| C12N 15/00 | (2006.01) |
| C12P 21/06 | (2006.01) |
| C12N 1/20 | (2006.01) |
| C12N 15/70 | (2006.01) |
| C07K 14/245 | (2006.01) |
| C12N 9/10 | (2006.01) |
| C12P 21/02 | (2006.01) |

(52) U.S. Cl.
CPC ............ *C12N 15/70* (2013.01); *C07K 14/245* (2013.01); *C12N 9/1051* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,304,472 A | 4/1994 | Bass et al. | |
| 5,789,199 A | 8/1998 | Joly et al. | |
| 6,117,679 A | 9/2000 | Stemmer | |
| 6,376,246 B1 | 4/2002 | Crameri et al. | |
| 6,586,182 B1 | 7/2003 | Patten et al. | |
| 7,199,233 B1 | 4/2007 | Jensen et al. | |
| 8,216,815 B2 | 7/2012 | McDaniel et al. | |
| 2008/0220990 A1 | 9/2008 | Fox | |
| 2009/0312196 A1 | 12/2009 | Colbeck et al. | |
| 2011/0212508 A1 | 9/2011 | Rao et al. | |

FOREIGN PATENT DOCUMENTS

| | | |
|---|---|---|
| EP | 1990416 A1 | 11/2008 |
| WO | 02/40679 A2 | 5/2002 |
| WO | 2013/096092 A1 | 6/2013 |
| WO | 2014/159850 A2 | 10/2014 |

OTHER PUBLICATIONS

Kimura et al. Regulation of phosphate regulon of *Escherichia coli*: Characterization of the promoter of the pstS gene. 1989. Molecular Genetics and Genomics. vol. 215, pp. 374-380.*
Altschul, S., et al., "Basic local alignment search tool," J. Mol. Biol., 215: 403-410 (1990).
Altschul, S.F., et al., "Gapped BLAST and PSI-BLAST: a new generation of protein database search programs," Nucleic Acids Res., 25(17):3389-3402 (1997).
Blanco, A.G., et al., ",Tandem Dna Recognition by PhoB, a Two-Component Signal Transduction Transcriptional Activator," Structure, 10:701-713 [2002].
Bookout, A.L., et al., "High Throughput Real-Time Quantitative Reverse Transcription PCR," Current Protocols in Molecular Biology, pp. 15.8.1-15.8.28 [2006].
Chenna, R., et al., "Multiple sequence alignment with the Clustal series of programs," Nucl. Acids Res., 31(13):3497-3500 [2003].
Datta, S., et al., "A set of recombineering plasmids for gram-negative bacteria," Gene, 379: 109-115 (2006).
Diniz, M.M.P., et al., "Fine-Tuning Control of phoBR Expression in Vibrio cholerae by Binding of PhoB to Multiple Pho Boxes," J. Bact., 193(24): 6929-6938 [2011].
Hsieh, Y.-J., et al., "Global regulation by the seven-component Pi signaling system," Curr. Opin. Microbiol., 13(2):198-203 [2010].
Henikoff, S., et al., "Amino acid substitution matrices from protein blocks," Proc. Natl. Acad. Sci. USA, 89:10915-10919 [1992].
Lübke, C., et al., "Analysis and optimization of recombinant protein production in *Escherichia coli* using the inducible pho A promoter of the *E. coli* alkaline phosphatase," Enz. Microb. Technol., 17(10):923-928 [1995].
Moyle, H.,et al., "Hierarchies of base pair preferences in the P22 and promoter," J. Bact., 173:1944-1950 [1991].

(Continued)

*Primary Examiner* — Channing S Mahatan
(74) *Attorney, Agent, or Firm* — Codexis, Inc.

(57) ABSTRACT

The present invention provides compositions and methods comprising a low-phosphate repressible promoter. In particular, the present invention provides a low-phosphate repressible promoter from *E. coli*.

7 Claims, 2 Drawing Sheets

(56) References Cited

OTHER PUBLICATIONS

Needleman, S., et al., "A general method applicable to the search for similarities in the amino acid sequence of two proteins," J. Mol. Biol. 48:443-453 (1970).
Notredame, C., et al., "T-COFFEE: A novel method for multiple sequence alignments," JNB, 302:205-217, [2000].
Pearson, W.R., "Improved tools for biological sequence comparison," Proc. Nat'l. Acad. Sci. USA, 85:2444-2448 (1988).
Smith, T., et al., "Comparison of Biosequences," Adv. Appl. Math, 2:482-489 (1981).
Yao, N., et al., "Modulation of a Salt Link Does Not Affect Binding of Phosphate to Its Specific Active Transport Receptor," Biochem., 35(7):2079-2085 [1996].

* cited by examiner

LOW-PHOSPHATE REPRESSIBLE PROMOTER

CROSS-REFERENCE TO RELATED APPLICATION

The present application is a national stage application filed under 35 USC §371 and claims priority to international application to PCT International Application No. PCT/US2014/025332, filed Mar. 13, 2014 which claims priority to US Provisional Application. Ser. No. 61/783,641, filed Mar. 14, 2013, both of which are incorporated by reference, in their entireties and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file CX5-130WO1_ST25.TXT, created Mar. 11, 2014, 32,178 bytes, machine format IBM-PC, MS-Windows operating system, is hereby incorporated by reference.

FIELD OF THE INVENTION

The present invention provides compositions and methods comprising a low-phosphate repressible promoter. In particular, the present invention provides a low-phosphate repressible promoter from E. coli.

BACKGROUND OF THE INVENTION

Various bacterial expression control DNA sequences have been used to control the expression of foreign (i.e., heterologous) polynucleotide by transformed bacteria, as well as control expression of homologous genes. Indeed, with advances in genetic engineering in recent years, it has become possible to produce proteins in economically desirable quantities using various organisms as host cells. Escherichia coli (E. coli) is widely employed as a host cell in protein production systems, as it has a short generation period of about 20 minutes and can utilize a variety of sugars to proliferate. Furthermore, a large number of plasmid vectors have been developed that are useful in E. coli. The rapid and stable industrial production of recombinant proteins has been achieved with host-vector systems employing E. coli as host cell. Nonetheless, there remains a need to better control bacterial gene expression, particularly in commercial process systems.

SUMMARY OF THE INVENTION

The present invention provides compositions and methods comprising a low-phosphate repressible promoter. In particular, the present invention provides a low-phosphate repressible promoter from E. coli. In some embodiments, the present invention provides methods for controlling the expression of at least one product of interest through the modulation effects of a low-phosphate repressible promoter as provided herein. Indeed, it is intended that the present invention provide advantages in the selective expression of genes of interest. In some embodiments, the present invention provides means to silence (i.e., "turn off") the expression of certain genes during the growth of a microbial culture, as desired.

The present invention provides recombinant microorganisms comprising a desired phenotype, wherein the desired phenotype is obtained by exposing the microorganisms to conditions of limited phosphate concentration. In some embodiments, the genome of the microorganism comprises at least one mutation that alters the phosphate sensitivity of the microorganism. In some further embodiments, the microorganism comprises at least one mutation in pstS. In some additional embodiments, the pstS mutation is selected from T10M, T10Y, D56S, and/or T139H. In some further embodiments, the pstS mutations are selected from T10M, T10Y, D56S, and/or T139H, wherein the amino acid positions are numbered with reference to SEQ ID NO:3. In some still further embodiments, the recombinant microorganism is present within a culture medium and the desired phenotype is obtained by the expression of at least one gene under the control of at least one heterologous regulatory sequence and the heterologous regulatory sequence responds to the phosphate concentration of the culture medium. In some embodiments, the microorganism comprises the Pho1 and/or Pho17 promoter. In some embodiments, the recombinant microorganism comprises the Pho1 sequence set forth in SEQ ID NO:4. In some additional embodiments, the recombinant microorganism comprises the Pho17 sequence set forth in SEQ ID NO:5. In some further embodiments, the recombinant microorganism comprises the Pho1 sequence set forth in SEQ ID NO:4 and/or the Pho17 sequence set forth in SEQ ID NO:5. In still some additional embodiments, the microorganism is E. coli.

The present invention also provides methods for producing at least one heterologous polypeptide, comprising culturing a recombinant microorganism comprising at least one polynucleotide sequence encoding at least one heterologous polypeptide in a culture medium comprising a low concentration of phosphate, such that at least one polynucleotide is expressed and at least one heterologous polypeptide is produced. In some embodiments, at least one heterologous polypeptide is encoded by a heterologous gene wherein the heterologous gene comprises at least one mutation in the regulatory region of the gene. In some embodiments, the methods further comprise the step of recovering at least one polypeptide. In some embodiments, the recombinant microorganism comprises at least one mutation in pstS. In some further embodiments, the pstS mutations are selected from T10M, T10Y, D56S, and/or T139H. In some further embodiments, the pstS mutations are selected from T10M, T10Y, D56S, and/or T139H, wherein the amino acid positions are numbered with reference to SEQ ID NO:3. In some additional embodiments, the recombinant microorganism comprises the Pho1 and/or Pho17 promoter(s). In some embodiments, the recombinant microorganism comprises the Pho1 sequence set forth in SEQ ID NO:4. In some further embodiments, the recombinant microorganism comprises the Pho17 sequence set forth in SEQ ID NO:5. In still some additional embodiments, the recombinant microorganism comprises the Pho1 sequence set forth in SEQ ID NO:4 and the Pho17 sequence set forth in SEQ ID NO:5. In some embodiments, the microorganism is E. coli. In some additional embodiments, the recombinant microorganism produces an increased yield of at least one heterologous polypeptide, as compared to a recombinant microorganism that does not comprise at least one repressible promoter. In some further embodiments, the recombinant microorganism produces an increased yield of at least one product, as compared to a recombinant microorganism that does not comprise a repressible promoter. In some embodiments, the product comprises at least one alcohol. In some further embodiments, at least one heterologous polypeptide is selected from eukaryotic and prokaryotic polypeptides.

The present invention also provides a low-phosphate repressible promoter comprising Pho1. In some embodiments, the Pho1 promoter comprises SEQ ID NO:4. In some additional embodiments, the present invention further provides a low-phosphate repressible promoter comprising Pho17. In some embodiments, the Pho17 promoter comprises SEQ ID NO:5.

The present invention further provides expression constructs comprising at least one low-phosphate repressible promoter. In some embodiments, the expression constructs comprise the Pho1 promoter and/or Pho17 promoter. In some further embodiments, the Pho1 promoter comprises SEQ ID NO:4. In some additional embodiments, the Pho17 promoter comprises SEQ ID NO:5.

The present invention also provides recombinant host cells comprising at least one low-phosphate repressible promoter, wherein the promoter is the low-phosphate repressible promoter Pho1 and/or Pho17. In some further embodiments, the Pho1 promoter comprises SEQ ID NO:4. In some additional embodiments, the Pho17 promoter comprises SEQ ID NO:5. In some embodiments, the host cell exhibits a desired phenotype.

DESCRIPTION OF THE INVENTION

Figure 1:
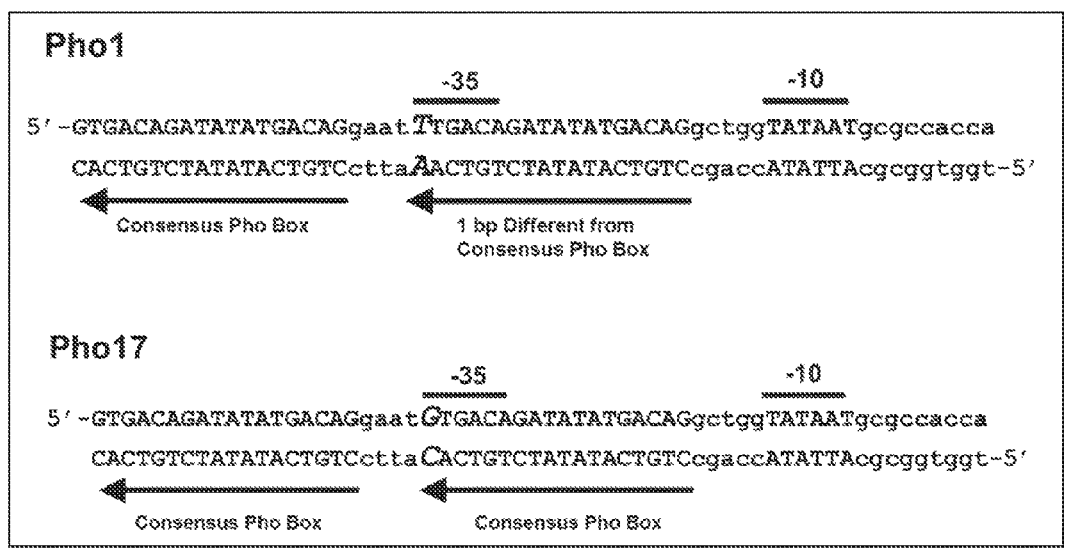
FIG. 1 provides partial DNA sequence of promoters Pho1 (SEQ ID NO:4) and Pho17 (SEQ ID NO:5). In this Figure, the arrows indicate the position and orientation of the Pho boxes according to Diniz et al. (Diniz et al., J. Bact. 193: 6929-6938 [2011]). The base changed in Pho17 is shown in italics. The −35 and −10 regions of the promoter are also indicated.

Proper control of gene expression is essential for the development of economically viable biotechnological commercial processes. A major consideration is that the cell's machinery is required to overproduce one and often more than one product in quantities that are commercially relevant. However, under normal circumstances, cells utilize various mechanisms that avoid the excessive production of any molecule that is not needed by the cell. One of these mechanisms is the tight regulation of gene expression, achieved by controlling activity of transcriptional promoters. A transcriptional promoter (herein referred as a "promoter"), is the region of the chromosome where the RNA polymerase binds, in order to initiate DNA transcription, thereby producing RNA capable of performing a biological function. Promoter activity is controlled by activation and/or repression mechanisms that enhance or decrease the promoter's capacity to drive RNA production. In most biotechnological processes utilizing E. coli as the production host, strong promoters are routinely used. These promoters are typically controlled by the binding of a repressor which inhibits the productive interaction of RNA polymerase with the promoter.

The most widely used promoter system in E. coli and other bacteria is the Lac promoter (Plac) and its repressor LacI. This system is commonly induced in the laboratory by the addition of the gratuitous inducer, isopropyl-beta-D-thio-galactosidase (IPTG). Another common expression system in E. coli is derived from the PhoA and PstS promoters, which are activated by the PhoB protein only when the level of phosphate (Pi) in the growth media is low. The use of phosphate as a way to modulate gene expression is particularly useful because phosphate is normally added to most growth media, and its levels can be easily controlled. In many bacteria, assimilation of phosphorus-containing compounds depends on the extracellular Pi concentration and is based on a sensing mechanism controlled by a two-component regulatory system. In E. coli and some other species, the system is encoded by the phoB and phoR genes. PhoR is a sensor histidine kinase that monitors the extracellular availability of phosphate, while PhoB is the response regulator that controls gene expression. The E. coli response to low-phosphate conditions involves PhoR autophosphorylation and the transfer of Pi to PhoB. Phosphorylated PhoB (PhoB~Pi) binds with higher affinity than non-phosphorylated PhoB to DNA and exerts its regulatory function on gene expression. In E. coli, PhoB~Pi activates the expression of a more than 40 genes (i.e., the Pho regulon) by binding to conserved 18-bp DNA sequences referred to as "Pho boxes" located upstream of the promoters of the Pho regulon genes (See e.g., Hasieh and Wanner. Curr. Opin. Microbiol., 13:198-203 [2010]). The E. coli consensus Pho box CT(G or T)TCAT A(A or T)A (A or T) CTGTCA(T OR C) (SEQ ID NO: 1) consist of two 7-bp directed repeats separated by a conserved 4-bp AT rich spacer (See, Blanco et al., Structure 10:701-713 [2002]; and Diniz et al., J. Bact., 193:6929-6938 [2011]).

As described herein, the use of a low-phosphate repressible promoter is useful when gene(s) need to be turned off (e.g., because their product is not needed) and/or the presence of the gene product interferes with the over-production of a desired product. Indeed, as described herein, the present invention provides new promoter systems for E. coli that can be repressed by low phosphate conditions.

In some additional embodiments, the phosphate sensor mechanism of a host cell is modified. Although it is not intended that the present invention be limited to any particular mechanism(s), mutations in the phosphate-binding pocket of the PstS sensor of E. coli can affect its affinity for phosphate and as a consequence, the sensitivity of the sensor mechanism (See e.g., U.S. Pat. No. 5,304,472; Yao et al., Biochem., 35:2079-2085 [1996]. Any suitable method for introducing mutations in the endogenous E. coli pstS gene find use in the present invention, including but not limited to oligonucleotide site-directed mutagenesis using the lambda RED recombineering technology as described herein. In some additional embodiments, mutations in one or more genes involved in the inorganic phosphate sensing mechanism (e.g., phoB, phoR, phoU pstsA, pstB, pstC, and/or pstS) find use in altering the phosphate sensitivity of host strains produced using the present invention. It is not intended that the present invention be limited to any particular mutations in any particular gene(s) nor any specific culture conditions. In some embodiments, the host strain is E. coli. Indeed, it is intended that the present invention find use in the production of any suitable heterologous polypeptide(s) by bacteria comprising at least one phosphate-repressible promoter of the present invention.

Definitions:

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry, and nucleic acid chemistry described below are well known and commonly employed in the art.

Such techniques are well-known and described in numerous texts and reference works well known to those of skill in the art. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole.

Also, as used herein, the singular "a", "an," and "the" include the plural references, unless the context clearly indicates otherwise. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein. Furthermore, the headings provided herein are not limitations of the various aspects or embodiments of the invention which can be had by reference to the application as a whole. Nonetheless, in order to facilitate understanding of the invention, a number of terms are defined below. Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

As used herein, the term "phosphate depletion" refers to a marked decrease in phosphate in the media, as compared to the phosphate concentration routinely used in culture media. As is known in the art, depending upon the E. coli strain used, the inoculum size, the initial phosphate concentration and the pH of the growth medium, the PhoB-PhoR system is induced when the phosphate concentration is below about 50 micromolar (See e.g., Lubke et al., Enz. Microb. Technol., 17:923-928 [1995]). However, it is also known that under some conditions, maximal induction is obtained when the phosphate concentration is less than about 4 micromolar (See e.g., Hasieh and Wanner, supra). Thus, it is not intended that the present invention be limited to any specific initial or process phosphate concentration, particular bacterial strain, or other growth conditions. Those of skill in the art understand how to modify the conditions to optimize the performance of the strain being used.

As used herein, "phosphate-binding region" is the region of a protein that binds to phosphate.

As used herein, the E. coli "PstS protein" refers to the protein encoded by the "PstS gene" in bacterial cells, including but not limited to the Enterobacteriaceae (e.g., E. coli). In some embodiments, the E. coli PstS comprises the following polypeptide and polynucleotide sequences, respectively:

(SEQ ID NO: 2)
MKVMRTTVATVVAATLSMSAFSVFAEASLTGAGATFPAPVYAKWADTYQK

ETGNKVNYQGIGSSGGVKQIIANTVDFGASDAPLSDEKLAQEGLFQFPTV

IGGVVLAVNIPGLKSGELVLDGKTLGDIYLGKIKKWDDEAIAKLNPGLKL

PSQNIAVVRRADGSGTSFVFTSYLAKVNEEWKNNVGTGSTVKWPIGLGGK

GNDGIAAFVQRLPGAIGYVEYAYAKQNNLAYTKLISADGKPVSPTEENFA

NAAKGADWSKTFAQDLTNQKGEDAWPITSTTFILIHKDQKKPEQGTEVLK

FFDWAYKTGAKQANDLDYASLPDSVVEQVRAAWKTNIKDSSGKPLY (SEQ ID No: 3)
atgAAAGTTATGCGTACCACCGTCGCAACTGTTGTCGCCGCGACCTTATC

GATGAGTGCTTTCTCTGTGTTTGCAGAAGCAAGCCTGACAGGTGCAGGTG

CAACCTTCCCTGCGCCGGTGTATGCCAAATGGGCTGACACTTACCAGAAA

GAAACCGGTAATAAAGTTAACTACCAGGGTATCGGTTCTTCCGGTGGCGT

AAAACAGATTATCGCTAATACCGTTGATTTTGGTGCCTCTGACGCGCCGC

TGTCTGACGAAAAACTGGCTCAGGAAGGTCTGTTCCAGTTCCCGACCGTG

ATTGGCGGCGTGGTGCTGGCGGTTAACATTCCAGGGCTGAAGTCTGGCGA

ACTGGTGCTGGATGGTAAAACCCTCGGCGACATCTACCTGGGCAAAATCA

AGAAGTGGGATGATGAAGCCATCGCCAAACTGAATCCGGGTCTGAAACTG

CCTTCACAAAACATTGCTGTAGTACGCCGCGCAGATGGCTCCGGGACTTC

CTTCGTCTTCACCAGCTACCTGGCGAAAGTGAACGAAGAGTGGAAAAACA

ACGTTGGTACTGGCTCTACCGTAAAATGGCCGATCGGTCTGGGCGGTAAA

GGTAACGACGGTATCGCCGCGTTCGTTCAGCGTCTGCCGGGTGCAATTGG

TTATGTTGAATATGCTTACGCGAAGCAGAACAACCTGGCGTACACCAAAC

TGATCTCCGCTGATGGTAAACCGGTTAGTCCGACCGAAGAAACTTCGCT

AATGCAGCAAAAGGTGCAGACTGGAGCAAAACCTTCGCTCAGGATCTGAC

CAACCAGAAAGGCGAAGATGCATGGCCTATTACCTCTACCACGTTCATTC

TGATCCACAAAGATCAGAAGAAACCAGAACAAGGCACAGAAGTGCTGAAA

TTCTTCGACTGGGCGTACAAAACCGGGGCTAAACAGGCGAACGACCTGGA

TTACGCCAGCCTGCCGGATAGTGTAGTTGAACAGGTTCGCGCTGCGTGGA

AGACCAATATTAAAGACAGTAGCGGTAAGCCGCTGTACtaa

As used herein, the terms "enzyme variant" and "variant enzyme," including "PstS variant" are used in reference to enzymes that are similar to a reference enzyme, particularly in their function, but have mutations in their amino acid sequence that make them different in sequence from the wild-type or another reference enzyme. Enzyme variants can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. After the variants are produced, they can be screened for any suitable desired property.

As used herein, the term "promoter" refers to transcriptional promoters (i.e., sequences that direct the transcription of polynucleotides).

As used herein, a "promoter sequence" is a nucleic acid sequence that is recognized by a host cell for expression of the coding region. The control sequence may comprise an appropriate promoter sequence. The promoter sequence contains transcriptional control sequences that mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either endogenous or heterologous to the host cell.

As used herein, "bacterial promoter" refers to a promoter that is capable of initiating transcription in bacterial cells. In some embodiments, the promoter is capable of modulating the transcription of at least one polynucleotide. In some embodiments, the bacterial promoter is an *E. coli* promoter.

As used herein, a "repressible promoter" is a promoter that exhibits a reduced capacity to function under certain conditions.

As used herein, a "phosphate-regulated promoter" is a transcriptional promoter, wherein the promoter's capacity to function is regulated by the phosphate level in the growth media used to culture the cells in which the promoter resides.

As used herein, "phosphate sensitivity" refers to the effects of phosphate in media on a phosphate-regulated promoter. In some embodiments, the promoters are relatively insensitive to the phosphate concentration (i.e., the phosphate concentration has no impact on the activity of the promoter), while in some other embodiments, the promoters are very sensitive to the phosphate concentration (i.e., the phosphate concentration greatly influences the activity of the promoter).

As used herein, a "low-phosphate-repressible promoter," is a transcriptional promoter, wherein the promoter's capacity to function is reduced under low-phosphate conditions, as compared to the promoter's functional capacity under conditions in which the phosphate in the growth medium used to culture the bacteria comprising the promoter is in high concentration, such as in growth media that are commonly used to culture bacteria.

As used herein, the term "low-phosphate conditions" refer to a phosphate concentration in growth media lower than about 50 micromolar.

As used herein, the term "inducible promoter" refers to a transcriptional promoter, wherein the promoter's capacity to function efficiently, requires the presence or absence of chemical or physical factors. Thus, in some embodiments, the inducible promoter's activity is influenced by certain conditions (e.g., light, temperature, chemical concentration, protein concentration, etc.).

As used herein, the term "constitutive promoter" refers to promoters that actively promote transcription under most, but not necessarily all environmental conditions and/or states of cell development and/or differentiation.

As used herein, "optional promoter fragments" refer to any sub-sequence(s) of a promoter that is/are not required for driving transcription of an operably linked coding region. In some embodiments, these fragments comprise the 5' UTR (i.e., 5' untranslated region), as well as any exon(s) of the endogenous coding region. In some further embodiments, optional promoter fragments comprise any exon(s) and the 3' or 5' of the gene residing upstream of the promoter (i.e., 5' to the promoter). The term also encompasses any intervening sequences (i.e., introns), as well as sequence that occurs between exons or an exon and the UTR.

As used herein, the term "preferential transcription" refers to transcription that occurs in response to specific stimuli (e.g., low or high phosphate concentrations). Preferential transcription can be assessed by measuring initiation, rate, and/or transcription levels.

As used herein, the term "modulate transcription" refers to the activity of a promoter sequence to affect up- and down-regulation of transcription initiation, rate of transcription, and/or transcription levels, as well as any other relevant biological activity.

As used herein, the term "transcription start site" refers to the point at which transcription is initiated on a polynucleotide.

As used herein, the term "phenotype" refers to the observable characteristics of a strain. These characteristics result from the expression of the strain's genes, as well as the influence of environmental factors and the interactions between the two. Examples of phenotypes include but are not limited to the growth rate of a strain under a particular set of conditions; the ability of a strain to use glucose as a carbon source; and/or the capability of a strain to express certain gene(s) under low-phosphate growth conditions.

As used herein, a "desired phenotype" is a particular phenotype that is obtained by at least one genetic modification of a strain. Thus, the desired phenotype is different from the strain's phenotype prior to the genetic modification(s). For example, in some embodiments, the starting (i.e., parent) strain is capable of expressing certain genes under low phosphate conditions and the desired phenotype is a strain unable to express such genes under the same growth conditions. In some additional embodiments, the parent strain is capable of expressing certain genes under high phosphate conditions and the desired phenotype is a strain unable to express such genes under the same growth conditions.

As used herein, "pathway" refers to a set of system components that are involved in at least two sequential interactions that result in the production of a product and/or activity. The term encompasses various pathway types, including but not limited to biochemical pathways, gene expression pathways, regulatory pathways, and/or a combination of these exemplary pathway types.

As used herein, the term "public sequence" refers to any sequence deposited in a publicly accessible database. The term encompasses amino acid and nucleotide sequences. Examples of publicly available databases include, but are not limited to the NCBI FTP website, GenBank, European Bioinformatics Institute (EBI-EMBL), DNA Database of Japan (DBBJ), and Brookhaven Protein Data Bank (PDB), as well as the databases associated with patent offices (e.g., the US Patent & Trademark Office).

The terms "polynucleotide" and "nucleic acid", used interchangeably herein, refer to a polymeric form of nucleotides of any length, either ribonucleotides or deoxyribonucleotides. These terms include, but are not limited to, single-, double- or triple-stranded DNA, genomic DNA, cDNA, RNA, DNA-RNA hybrid, polymers comprising purine and pyrimidine bases, and/or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and/or nucleotide branches. In some alternative embodiments, the sequence of nucleotides is interrupted by non-nucleotide components.

As used herein, the terms "DNA construct" and "transforming DNA" are used interchangeably to refer to DNA that is used to introduce sequences into a host cell or organism. The DNA may be generated in vitro by PCR or any other suitable technique(s) known to those in the art. In some embodiments, the DNA construct comprises a sequence of interest (e.g., as an "incoming sequence"). In some embodiments, the sequence is operably linked to additional elements such as control elements (e.g., promoters, etc.). In some embodiments, the DNA construct further comprises at least one selectable marker. In some further embodiments, the DNA construct comprises an incoming sequence flanked by homology boxes. In some further embodiments, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In some other embodiments, the DNA construct comprises non-homologous sequences. Once the DNA construct is assembled in vitro, it may be used to: 1) insert heterologous sequences into a desired target sequence of a host cell; 2) mutagenize a region of the host cell chromosome (i.e., replace an endogenous sequence with a heterologous sequence); 3) delete target genes; and/or 4) introduce a replicating plasmid into the host. In some embodiments, the incoming sequence comprises at least one selectable marker. This sequence can code for one or more proteins of interest. It can have other biological functions. In many cases the incoming sequence comprises at least one selectable marker, such as a gene that confers antimicrobial resistance.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette/vector includes, among other sequences, a nucleic acid sequence to be transcribed and a promoter. In some embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the enzyme (e.g., precursor or mature enzyme) that is operably linked to a suitable prosequence capable of effecting the expression of the DNA in a suitable host.

As used herein, "a secretion signal peptide" can be a propeptide, a prepeptide or both. For example, the term "propeptide" refers to a protein precursor that is cleaved to yield a mature protein. The term "prepeptide" refers to a polypeptide synthesized with an N-terminal signal peptide that targets it for secretion. Accordingly, a "pre-pro-peptide" is a polypeptide that contains a signal peptide that targets the polypeptide for secretion and which is cleaved off to yield a mature polypeptide. Signal peptides are found at the N-terminus of the protein and are typically composed of between about 3 to about 136 basic and hydrophobic amino acids.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, transduction, and electroporation.

As used herein, the terms "transformed" and "stably transformed" refers to a cell that has a non-native (i.e., heterologous) polynucleotide sequence integrated into its genome or as an episomal plasmid that is maintained for at least two generations.

As used herein, the terms "control sequences" and "regulatory sequences" refer to nucleic acid sequences necessary and/or useful for expression of a polynucleotide encoding a polypeptide. In some embodiments, control sequences are native (i.e., from the same gene) or foreign (i.e., from a different gene) to the polynucleotide encoding the polypeptide. Control sequences include, but are not limited to leaders, polyadenylation sequences, propeptide sequences, promoters, signal peptide sequences, and transcription terminators. In some embodiments, at a minimum, control sequences include a promoter, and transcriptional and translational stop signals. In some embodiments, control sequences are provided with linkers for the purpose of introducing specific restriction sites facilitating ligation of the control sequences with the coding region of the polynucleotide encoding the polypeptide.

As used herein, "operably linked" refers to a configuration in which a control sequence is appropriately placed (i.e., in a functional relationship) at a position relative to a polynucleotide of interest such that the control sequence directs or regulates the expression of the polynucleotide and/or polypeptide of interest. Thus, a nucleic acid is "operably linked" to another nucleic acid sequence when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Inactive" or "inactivated" in reference to a gene refers to a gene having at least one function that is impaired. Genes can be inactivated in a variety of ways known in the art, including but not limited to insertion of a mobile genetic element (e.g., a transposon); deletion of all or part of the gene, such that the gene product is not made, or is truncated and is non-functional; mutation of the gene such that the gene product is not made, or is truncated and is non-functional; deletion or mutation of one or more control elements that control expression of the gene such that the gene product is not made; and the like. In certain embodiments genes can be inactivated by methods other than genetic modification, for example, by gene silencing at the transcriptional level or at the post-transcriptional level using for example RNAi.

"Recombinant host cell" refers to a cell into which has been introduced a heterologous polynucleotide, gene, promoter, e.g., an expression vector, or to a cell having a heterologous polynucleotide or gene integrated into the genome.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation. A wild-type organism refers to an organism that has not been intentionally modified by human manipulation.

As used herein the term "transformed" or "transformation" used in reference to a cell means a cell has a non-native nucleic acid sequence integrated into its genome or as a plasmid that is maintained through multiple generations.

As used herein the term "gene" refers to a polynucleotide (e.g., a DNA segment), that encodes a polypeptide and includes regions preceding and following the coding regions as well as intervening sequences (introns) between individual coding segments (exons).

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology-Hybridization with Nucleic Acid Probes*." Part 1, Chapter 2, Elsevier, New York, [1993], incorporated herein by reference). For polynucleotides of at least 100 nucleotides in length, low to very high stringency conditions are defined as follows: prehybridization and hybridization at 42° C. in 5×SSPE. 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. ("low" stringency), at least at 55° C. ("medium" or "moderate" stringency), at least at 60° C. ("medium-high" stringency), at least at 65° C. ("high" stringency), and at least at 70° C. ("very high" stringency). In some embodiments, the stringency conditions include those that: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. In other embodiments, the stringency conditions include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors to accomplish the desired stringency.

As used herein, an "endogenous" or "homologous" gene refers to a gene that is found in a parental strain of a cell (e.g., a bacterial cell). In some embodiments, endogenous genes are present in wild-type strains. As used herein in making comparisons between nucleic acid sequences, "homologous genes" (or "homologue" genes) refers to genes from different, but usually related species, that correspond to each other and are identical or very similar to each other. The term encompasses genes that are separated by speciation (i.e., the development of new species) (e.g., orthologous genes), as well as genes that have been separated by genetic duplication (e.g., paralogous genes).

As used herein, "heterologous" polynucleotides are any polynucleotides that are introduced into a host cell through the use of laboratory techniques/manipulation, and include polynucleotides that are removed from a host cell, subjected to laboratory manipulation, and then reintroduced into a host cell.

As used herein, when used with reference to a nucleic acid or polypeptide, the term "heterologous" refers to a sequence that is not normally expressed and secreted by an organism (e.g., a "wild-type" organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector).

As used herein, a "heterologous enzyme" is used in reference to an enzyme that is encoded by a heterologous gene. However, it is also contemplated herein that a heterologous gene can encode an endogenous or homologous enzyme. As used herein, the term "heterologous gene" refers to a gene that occurs in a form not found in a parental strain of the cell. Thus, in some embodiments, a heterologous gene is a gene that is derived from a species that is different from the species of the cell expressing the gene and recognized anamorphs, teleomorphs or taxonomic equivalents of the cell expressing the gene. In some embodiments, a heterologous gene is a modified version of a gene that is endogenous to the host cell (e.g., an endogenous gene subjected to manipulation and then introduced or transformed into the host cell). For example, in some embodiments, a heterologous gene has an endogenous coding sequence, but has modifications in the promoter sequence. Similarly, in other embodiments, a heterologous gene encodes the same amino acid sequence as an endogenous gene, but has modifications in codon usage and/or to noncoding regions (e.g., introns), and/or combinations thereof. For example, in some embodiments, a heterologous gene contains modifications to the coding sequence to encode a non-wild-type polypeptide. As another example, in some embodiments, a heterologous gene has the same promoter sequence, 5' and 3' untranslated regions and coding regions as a parental strain, but is located in another region of the same chromosome, or on an entirely different chromosome as compared to a parental strain of the host cell. In some embodiments, the heterologous gene is a gene that has been modified to overexpress a gene product of interest.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (i.e., non-recombinant) form of the cell or express native genes that are otherwise abnormally expressed, under-expressed or not expressed at all as a result of deliberate human intervention. "Recombinant," "engineered," and "non-naturally occurring," when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (i.e., non-recombinant) form of the cell or express native genes that are otherwise expressed at a different level. "Recombination," "recombining," and "generating a recombined" nucleic acid also encompass the assembly of two or more nucleic acid fragments wherein the assembly gives rise to a chimeric gene.

As used herein, a "genetically modified" or "genetically engineered" cell is a cell whose genetic material has been altered using genetic engineering techniques. A genetically modified cell also refers to a derivative of or the progeny of a cell whose genetic material has been altered using genetic engineering techniques. An example of a genetic modification as a result of genetic engineering techniques includes a modification to the genomic DNA. Another example of a genetic modification as a result of genetic engineering techniques includes introduction of a stable heterologous nucleic acid into the cell.

As used herein, the term "expression" refers to the any step involved in the production of at least one polypeptide of interest, including but not limited to transcription and translation.

As used herein, the term "overexpression" refers to any state in which a gene is caused to be expressed at an elevated rate or level as compared to the endogenous expression rate or level for that gene. In some embodiments, "overexpression" includes an elevated translation rate or level of the gene compared to the endogenous translation rate or level for that gene. In some embodiments, overexpression includes an elevated transcription rate or level of the gene compared to the endogenous transcription rate or level for that gene. For example, in some embodiments, a heterologous gene is introduced into a cell to express a gene encoding a heterologous protein enzyme (e.g., beta-glucosidase or any other suitable enzyme or protein of interest) from another organism. In some other embodiments, a heterologous gene is introduced into a cell to overexpress a gene encoding a homologous enzyme such as a fatty alcohol reductase.

As used herein, the terms "amplification" and "gene amplification" refer to a method by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, that is capable of acting as a synthesis initiation point when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. As known in the art, the exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" (PCR) refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This method for amplifying the target sequence is well known in the art.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In some embodiments of the invention, restriction sites are engineered into the selective marker and into 5' and 3' ends of the DNA construct.

As used herein, "homologous recombination" means the exchange of DNA fragments between two DNA molecules or paired chromosomes at the site of identical or nearly identical nucleotide sequences. In some embodiments, chromosomal integration is homologous recombination.

As used herein "amino acid" refers to peptide or protein sequences or portions thereof. The terms "protein," "peptide," and "polypeptide" are used interchangeably in reference to a polymer of amino acid residues). The term "amino acid" refers to naturally occurring and synthetic amino acids, as well as amino acid analogs. Naturally occurring amino acids are those encoded by the genetic code, as well as those amino acids that are later modified (e.g., hydroxyproline, γ-carboxyglutamate, and O-phosphoserine). "The term amino acid analogs" refers to compounds that have the same basic chemical structure as a naturally occurring amino acid (i.e., an α-carbon that is bound to a hydrogen, a carboxyl group, an amino group, and an R group, such as homoserine, norleucine, methionine sulfoxide, or methionine methyl sulfonium). Such analogs have modified R groups (e.g., norleucine) or modified peptide backbones, but retain the same basic chemical structure as a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. It is also understood that a polypeptide may be encoded by more than one nucleotide sequence, due to the degeneracy of the genetic code.

A used herein, an amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

As used herein, the terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, "conservative substitution," as used with respect to amino acids, refers to the substitution of an amino acid with a chemically similar amino acid. Amino acid substitutions that do not generally alter specific activity are well known in the art and are described in numerous textbooks.

The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these in reverse. In some embodiments herein, a conservative substitute for a residue is another residue in the same group as shown in the Table below.

| | |
|---|---|
| basic amino acids | arginine (R), lysine (K), histidine (H) |
| acidic amino acids | glutamic acid (E), aspartic acid (D) |
| polar amino acids | glutamine (Q), asparagine (N) |
| hydrophobic amino acids | leucine (L), isoleucine (I), valine (V) |
| aromatic amino acids | phenylalanine (F), tryptophan (W), tyrosine (Y) |
| small amino acids | glycine (G), alanine (A), serine (S), threonine (T), proline (P), cysteine (C), methionine (M) |

In some embodiments, "conservative" amino acid substitutions or mutations refer to the interchangeability of residues having similar side chains, and thus typically involves substitution of the amino acid in the polypeptide with amino acids within the same or similar defined class of amino acids. However, as used herein, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein. A, V, L, or I can be conservatively mutated to either another aliphatic residue or to another non-polar residue. The following table provides exemplary conservative substitutions.

| Residue | Possible Conservative Mutations |
|---|---|
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar (N, Q, S, T) |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

The following nomenclature may be used to describe substitutions in a reference sequence relative to a reference sequence or a variant polypeptide or nucleic acid sequence: "R-#-V," where "#" refers to the position in the reference sequence, "R" refers to the amino acid (or base) at that position in the reference sequence, and "V" refers to the amino acid (or base) at that position in the variant sequence.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions.

As used herein, "deletion" when used in reference to a polypeptide, refers to modification of the polypeptide by removal of one or more amino acids from a reference polypeptide. Deletions can comprise removal of 1 or more amino acids, 2 or more amino acids, 3 or more amino acids, 4 or more amino acids, 5 or more amino acids, 6 or more amino acids, 7 or more amino acids, 8 or more amino acids, 9 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered at least one protease enzyme. Deletions may be present in the internal portions and/or terminal portions of the polypeptide. In some embodiments, the deletion comprises a continuous segment, while in other embodiments, it is discontinuous.

As used herein, a "gene deletion" or "deletion mutation" is a mutation in which at least part of a sequence of the DNA making up the gene is missing. Thus, a "deletion" in reference to nucleic acids is a loss or replacement of genetic material resulting in a complete or partial disruption of the sequence of the DNA making up the gene, including its regulatory sequences involved in DNA transcription and RNA translation. Any number of nucleotides can be deleted, from a single base to an entire piece of a chromosome. Thus, in some embodiments, the term "deletion" refers to the removal of a gene necessary for encoding a specific protein (e.g., a protease). In this case, the strain having this deletion can be referred to as a "deletion strain."

"Insertion" refers to modification to the polypeptide by addition of one or more amino acids to the reference polypeptide. In some embodiments, the modification comprises insertions of one or more amino acids to the naturally occurring polypeptide as well as insertions of one or more amino acids to other modified polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide. The term "insertion" is also used to refer to a DNA modification in which or more nucleotides or nucleotide base-pairs have been inserted, as compared to the corresponding reference, parental or "wild type" DNA.

As used herein, the phrases "different from" and "differs from" when used with respect to a designated reference sequence refers to difference of a given amino acid or polynucleotide sequence when aligned to the reference sequence. Generally, the differences can be determined when the two sequences are optimally aligned. Differences include insertions, deletions, or substitutions of amino acid residues in comparison to the reference sequence.

As used herein in the context of a polypeptide or polynucleotide, the phrase "derived from" a particular organism refers to a wild-type polynucleotide or polypeptide that originates in the organism and to mutant and variants thereof that either originate in the organism or are produced by human manipulation of the wild-type polynucleotide or polypeptide.

"Functional fragment" as used herein refers to a polypeptide that has an amino-terminal and/or carboxy-terminal deletion, but where the remaining amino acid sequence is identical to the corresponding positions in the sequence and that retains substantially all of the activity of the full-length polypeptide. Functional fragments can comprise up to about 60%, about 65%, about 70%, about 75%, about 80%, about 85%, about 90%, about 91%, about 92%, about 93%, about 94%, about 95%, about 96%, about 97%, about 98%, or about 99% of the full-length polypeptide.

"Percentage of sequence identity," "percent identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which may also contain gaps to optimize the alignment) for alignment of the two sequences. The percentage may be calculated by determining the number of positions at which the identical nucleic acid base or amino acid residue occurs in both sequences to yield the number of matched positions, dividing the number of matched positions by the total number of positions in the window of comparison (including positions where one of the sequences has a gap) and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences and that different methods may give slightly different results.

Alignment of sequences for comparison can be conducted, e.g., by the local homology algorithm of Smith and Waterman (See, Smith and Waterman, Adv. Appl. Math., 2:482 [1981]), by the homology alignment algorithm of Needleman and Wunsch, (See, Needleman and Wunsch, J. Mol. Biol., 48:443 [1970]), by the search for similarity method of Pearson and Lipman (See, Pearson and Lipman, Proc. Natl. Acad. Sci. USA 85:2444 [1988]), by computerized implementations of these algorithms (GAP, BESTFIT, FASTA, and TFASTA in the GCG Wisconsin Software Package), or by visual inspection, using methods known in the art. In some embodiments, the Clustal (See, Chenna et al., Nucl. Acids Res., 31:3497-3500 [2003]) and T-Coffee (See, Notredame et al., J. Mol. Biol., 302:205-217 [2000]) software packages find use in aligning sequences.

Examples of algorithms that are suitable for determining percent sequence identity and sequence similarity are the BLAST and BLAST 2.0 algorithms (See e.g., Altschul et al., J. Mol. Biol., 215:403-410 [1990]; and Altschul et al., Nucl. Acids Res., 25:3389-3402 [1977], respectively). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (See, Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues: always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value: the cumulative score goes to zero or below, due to the accumulation of one or more negative-scoring residue alignments: or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See, Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "substrate" refers to a substance or compound that is converted or designated for conversion into another compound (e.g., a product) by the action of an enzyme. The term includes not only a single compound but also combinations of compounds, such as solutions, mixtures and other materials which contain at least one substrate.

As used herein, "conversion" refers to the enzymatic transformation of a substrate to the corresponding product. "Percent conversion" refers to the percent of the substrate that is converted to the product within a period of time under specified conditions. Thus, the "enzymatic activity" or "activity" of a polypeptide can be expressed as "percent conversion" of the substrate to the product.

As used herein, "culturing" and "cultivation" refer to growing a population of microbial cells under suitable conditions in a liquid, solid or semi-solid medium. In some embodiments, culturing refers to the fermentative bioconversion of a substrate to an end-product. Culturing media are well known and individual components of such culture media are available from various commercial sources (e.g., Difco® and BBL® media). In one non-limiting example, the aqueous nutrient medium is a "rich medium" comprising complex sources of nitrogen, salts, and carbo, such as YP medium, comprising 10 g/L of peptone and 10 g/L yeast extract of such a medium.

In some embodiments, cells are grown under batch or continuous fermentations conditions.

"Continuous culturing" is an open system in which a culture medium (typically, a defined culture medium) is added continuously to a bioreactor and an equal amount of conditioned medium is removed simultaneously for processing. Continuous culturing generally maintains the cultures at a constant high density where cells are primarily in log phase growth. Continuous culturing systems strive to maintain steady state growth conditions. Methods for modulating nutrients and growth factors for continuous culturing processes as well as techniques for maximizing the rate of product formation are well known in the art of industrial microbiology.

Combinations and/or variations of unique characteristics of these processes find use in various embodiments of the present invention. Indeed, it is not intended that the present invention be limited to any specific growth protocol and/or method. Classical "batch culturing" involves a closed system, wherein the composition of the medium is set at the beginning of the culture process and is not subject to artificial alternations during the culture process. A variation of the batch system is "fed-batch culturing" which also finds use in the present invention. In this variation, the substrate is added in increments as the culturing process progresses. Fed-batch systems are useful when catabolite repression is likely to inhibit the metabolism of the cells and where it is desirable to have limited amounts of substrate in the medium. Batch and fed-batch cultures are common and well known in the art. In some additional embodiments, "repeated fed-batch" culturing finds use in the present invention. In these methods, the feed (i.e., comprising at least one carbon source) is added in increments as the culturing process progresses. When the broth volume reaches a predefined working volume of the culture vessel, a portion of the broth is removed, generating new vessel capacity to accommodate further carbon source feeding. The repeated fed-batch systems are useful to maximize culture vessel capacity and enable the production of more total product than the standard fed-batch process.

As used herein, "fed-batch method" refers to a method by which a fed-batch culture or repeated fed-batch culture is supplied with additional nutrients. For example, in some embodiments, fed-batch methods (including repeated fed-batch methods) comprise adding supplemental media according to a determined feeding schedule within a given time period.

In some embodiments, fermentations are carried out a temperature within the range of from about 10° C. to about 60° C., from about 15° C. to about 50° C., from about 20° C. to about 45° C., and from about 25° C. to about 40° C. In some embodiments, the fermentation is carried out at a temperature of from about 28° C. and also from about 30° C. In some other embodiments, the fermentation is carried out for a period of time within the range of from about 8 hours to 240 hours, from about 8 hours to about 168 hours, from about 16 hours to about 144 hours, from about 16 hours to about 120 hours, or from about 24 hours to about 72 hours. It will be understood that, in certain embodiments where thermostable host cells are used, fermentations may be carried out at higher temperatures. In other embodiments, the fermentation will be carried out at a pH in the range of 4 to 8, in the range of 4.5 to 7.5, in the range of 5 to 7, and also in the range of 5.5 to 6.5.

Carbon sources useful in the aqueous fermentation medium or broth of the disclosed process in which the recombinant microorganisms are grown are those assimilable by the recombinant host strain. Assimilable carbon sources are available in many forms and include renewable carbon sources and the cellulosic and starch feedstock substrates obtained there from. Such examples include for example monosaccharides, disaccharides, oligosaccharides, saturated and unsaturated fatty acids, succinate, acetate and mixtures thereof. Further carbon sources include, without limitation, glucose, galactose, sucrose, xylose, fructose, glycerol, arabinose, mannose, raffinose, lactose, maltose, and mixtures thereof. In some embodiments, the term "fermentable sugars" is used interchangeably with the term "assimilable carbon source." In some embodiments, fermentation is carried out with a mixture of glucose and galactose as the assimilable carbon source. In another aspect, fermentation is carried out with glucose alone to accumulate biomass, after which the glucose is substantially removed and replaced with an inducer (e.g., galactose for induction of expression of one or more heterologous genes involved in fatty alcohol production). In some other embodiments, fermentation is carried out with an assimilable carbon source that does not mediate glucose repression (e.g., raffinose), to accumulate biomass, after which the inducer (e.g., galactose), is added to induce expression of one or more heterologous genes involved in fatty alcohol production. In some embodiments, the assimilable carbon source is from cellulosic and starch feedstock derived from but not limited to, wood, wood pulp, paper pulp, grain, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass and mixtures thereof.

As used herein, the term "inducer" refers to any molecule or compound that positively influences the over-production of any protein (e.g., enzyme) over the corresponding basal level of production.

As used herein, the term "inducer-free" media refers to media that lack any inducer molecule or compound, while the term "inducer-containing" media refers to media that comprise one or more inducers.

As used herein, the term "alcohol" refers to any compound comprising at least hydroxyl group. In some embodiments, the term encompasses compounds comprising carbon chain lengths of about one to about twenty. In some additional embodiments, the term encompasses compounds comprising carbon lengths greater than twenty. In some further embodiments, the term encompasses, but is not limited to ethanol, methanol, butanol, propanal, fatty alcohols, etc. Indeed, it is intended that the term encompass any compound comprising at least one hydroxyl group, including but not limited to compounds that comprise other constituents.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM and mmol (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); slp (standard liters per minute); MW (molecular weight): rpm (rotations per minute); ° C. (degrees Centigrade); OD (optical density); DNA (deoxyribonucleic acid): RNA (ribonucleic acid): FAR (fatty alcohol reductase); GC-FID (gas chromatography-flame ionization detector); GC-MS (gas chromatography-mass spectroscopy); HPLC (high pressure liquid chromatography); MIBK (methyl isobutyl ketone); PHUSION® (PHUSION® is a registered trademark of Thermo Fisher Scientific. Inc., Waltham, Mass.); Thermo Scientific (Thermo Scientific, Wilmington, Del.); BDH (BDH Chemicals, available from VWR International, LLC, Radnor, Pa.); Roche (Roche Applied Science, Pleasanton, Calif.); FIOPC (fold improvements over positive control); ARS (ARS Culture Collection or NRRL Culture Collection, Peoria, Ill.); ATCC (American Type Culture Collection, Manassas, Va.); ADM (Archer Daniels Midland. Decatur, Ill.); Axygen (Axygen, Inc., Union City, Calif.); GenScript (GenScript, USA Inc., Piscataway, N.J.); CGSC (E. coli Genetic Stock Center, Yale University, New Haven, Conn.); HERCULASE® is a registered trademark of Agilent Technologies (Agilent Technologies. Santa Clara, Calif.); (Dual Biosystems (Dual Biosystems AG, Schlieven, Switzerland); Megazyme (Megazyme International Ireland, Ltd., Wicklow, Ireland); Sigma-Aldrich (Sigma-Aldrich, St. Louis, Mo.); BASF (BASF Aktiengesellschaft Corp., Ludwigshafen, Del.); Dasgip (Dasgip Biotools. LLC, Shrewsbury, Mass.); Difco (Difco Laboratories, BD Diagnostic Systems, Detroit, Mich.); PCRdiagnostics (PCRdiagnostics, by E coli SRO, Slovak Republic); Agilent (Agilent Technologies, Inc., Santa Clara, Calif.); Molecular Devices (Molecular Devices, Sunnyvale, Calif.); Symbio (Symbio, Inc., Menlo Park, Calif.); Newport (Newport Scientific. Australia); Bio-Rad (Bio-Rad Laboratories, Hercules, Calif.); Qiagen (Qiagen Sciences Inc., Germantown, Mass.); Zymo (Zymo Research Corporation. Irvine, Calif.); Promega (Promega Corporation, Madison, Wis.); Invitrogen (Invitrogen, Inc., Carlsbad, Calif.); NEB (New England BioLabs, Ipswich, Mass.); Sensient (Sensient Bio-Ingredients, Indianapolis, Ind.); Alfa Aesar (Alfa Aesar, Ward Hill, Mass.); Calbiochem (EMD Biosciences Inc., San Diego, Calif.); Mallinckrodt (Mallinckrodt Baker Inc. St. Louis, Mo., now Avantor Performance Materials, Center Valley, Pa.); JT Baker Mallinckrodt Baker Inc., St. Louis, Mo., now Avantor Performance Materials, Center Valley, Pa.); (Corn Products (Corn Products International, Stockton, Calif.); Richman Chemical (Richman Chemical Inc., Lower Gwynedd, Pa.); Omnipur (Omnipur, Caldwell, Id.; available from EMD Biosciences Inc., San Diego, Calif.); AMRESCO (AMRESCO LLC, Solon, Ohio); Michrom (Michrom Bioresources, Inc., Auburn, Calif.); LB (Luria-Bertani); LA (Luria-Bertani Agar); SOC (Super Optimal broth with Catabolite repression); and TB (Terrific Broth).

One method for quantification of total fatty alcohols and each one of the different chain lengths used cells were collected by centrifugation for 10 minutes at 6000 rpm in F15B-8×50C rotor. The cell pellets were resuspended in 0.5 mL of 6.7% Na$_2$SO$_4$ and then extracted with 1 mL of isopropanol:methyl t-butyl ether (4/6 ratio) for 2 hrs. The extract was centrifuged and analyzed either directly by GC-FID or GC-MS or derivatized with BSTFA before analysis. For derivatization, a 400 µL sample was taken off the top organic layer, evaporated under a nitrogen stream and the residue was derivatized with 100 µL N,O-Bis (trimethylsilyl)trifluoroacetamide) (BSTFA) at 37° C. for 1 hour, and then diluted with 100 µL of heptanes before analysis by GC-FID or GC-MS. 0.5 mL of the culture medium (after removal of cells by centrifugation) was also extracted with 1 mL methyl t-butyl ether for 1 hr. The organic phase was either analyzed directly by GC-FID or GC-MS or derivatized with BSTFA as described above before analysis. In addition, 0.5 mL of the cell culture (before removal of cells by centrifugation) was directly extracted with 1 mL of isopropanol:hexane (4:6 ratio) for 2 hrs. The organic phase was either analyzed directly by GC-FID or GC-MS or derivatized with BSTFA as described above before analysis.

A 1 µL sample was analyzed by GC-FID with the split ratio 1:10 using the following conditions: GC-6890N from Agilent Technologies equipped with FID detector and HP-5 column (length 30 m, I.D. 0.32 mm, film 0.25 um). GC method: start at 100° C., increase the temperature with a rate of 25° C./min to 246° C. and hold for 1.96 min. Total run time, 7.8 min. Under the above GC conditions the approximate retention times (min) of produced fatty alcohols and acids are as follows: 5.08, C14:0-OH; 5.40; C14:0-OOH; 5.74, C16:1-OH; 5.93, C16:0-OH; 6.11, C16:0-OOMe (internal standard); 6.16, C16:1-OOH; 6.29. C16:0-OOH; 6.80, C18:1-OH; 6.90, C18:0-OH; 7.3, C18:0- and C18:1-OOH. Identification of individual fatty alcohol was done by comparison to commercial standards (Sigma).

Example 1

Design and Cloning of the Synthetic Promoter Pho1

This Example describes the design and cloning of an *E. coli* synthetic promoter containing two PhoB-binding sites (PhoB boxes). In this construct, one of these PhoB boxes overlaps with the −35 region of the promoter, this PhoB box is referred to herein as the "Pho1 promoter." Other features included of this design included: an upstream transcriptional terminator to isolate the promoter from transcription of upstream promoter(s); consensus −35 and −10 regions to enhance RNA polymerase binding; 27 bp derived from P1 promoter from the rrnB gene to facilitate transcription initiation; 71 bp derived from rrnB gene, containing the anti-termination signals; 73 bp containing signals to enhance message RNA translation: and regions of homology to the lacI-LacZ genes.

The nucleotide sequence of the synthetic promoter's DNA is provided below:

(SEQ ID NO: 4)
CCAGCGTGGACCGCTTGCTGCAACTCTCTCAGGGCCAGGCGGTGAAGGGC

AATCAGCTGTTGCCCGTCTCACTGGTGAAAAGAAAAACCACCCTGGCGCC

CAATACGCAAACCGCCTCTCCCCGCGCGTTGGCCGATTCATTAATGCAGC

TGGCACGACAGGTTTCCCGACTGGAAAGCGGGCAGTAATAAAAATGCCAG

CCGATCGGGCTGGCATTTTTGCCTTTAAATTGGTTTGACAGCTTATCATC

GACTGCACGGTGCACCAATGCTTCTGGCGTCAGGCAGCCATCGGAAGCTG

TGGTATGGCTGTGCAGGTCGTAAATCACTGCATAATTCGTGTCGCTCAAG

GCGCACTCCCGTTCTGGATAATGTTTTTTGCGCCGACATGTTTGTGACAG

ATATATGACAGGAATTTGACAGATATATGACAGGCTGGTATAATGCGCCA

CCACTGACACGGAACAACGGCGCGCCGCTGAGAAAAAGCGAAGCGGCACT

GCTCTTTAACAATTTATCAGACAATCTGTGTGGGCACTCGACCGGAATTA

TCGATTAACTTTATTATTAAAAATTAAAGAGGTATATATTAATGTATCGA

TTAAATAAGGAGGAATAAACCATGACCATGATTACGGATTCACTGGCCGT

CGTTTTACAACGTCGTGACTGGGAAAACCCTGGCGTTACCCAACTTAATC

GCCTTGCAGCACATCCCCCTTTCGCCAGCTGGCGTAATAGCGAAGAGGCC

CGCACCGATCGCCCTTCCCAACAGTTGCGCAGCCTGAATGGCGAATGGCG

CTTTGCCTGGTTTCCGGC

This synthetic DNA was synthesized and cloned by GenScript in a pJETI-2 plasmid into the EcoRV site.

Example 2

Construction of a DNAS Cassette to Control fabB with the Pho1 Promoter

Figure 2:
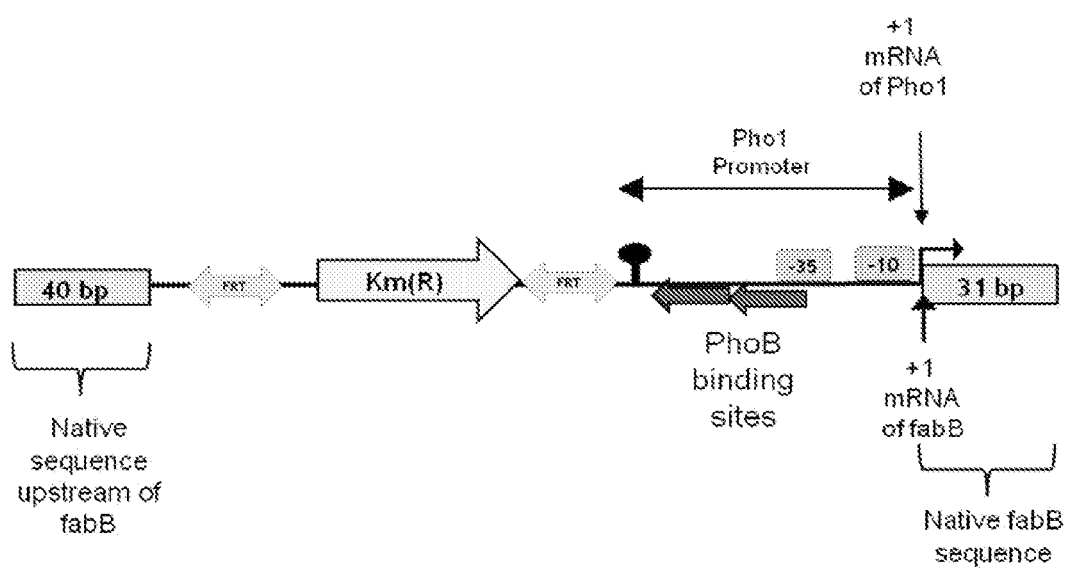
FIG. 2 provides a schematic showing the construction of a kanamycin-Pho1 promoter cassette as described in Example 2.

This Example describes the construction of a DNAS cassette to control fabB with the Pho1 promoter. This promoter cassette was designed to modulate the expression level of fabB based on the phosphate levels in the media by replacing the fabB native regulatory region with the kanamycin-Pho1 promoter cassette. This cassette contained 40 bp and 31 bp of regions of homology to the *E. coli* fabB gene, as well as the Pho1 promoter and a kanamycin resistance gene flanked by FLP recombinase target sites ("FRT sites") as shown in FIG. 2. The presence of the FRT sites facilitates removal of the Km marker by the action of the FLP recombinase.

This cassette was assembled by PCR in 3 steps using the Pho1-promoter cloned in pJETI described in Example 1. The following primers and conditions were used to obtain this cassette.

In the first step, the forward oligo (5' CDX-Pho1 F) (SEQ ID NO:9) containing 33 bases of homology to the kanamycin cassette (including an FRT site) and the reverse oligo (3' CDX Pho R) (SEQ ID NO:10) containing 40 bases of homology to the native fabB ribosome binding site RBS and 5' sequence of the FabB chromosomal gene were used. The sequences are shown below. The expected PCR product was 340 base pairs in length.

5' CDX-Pho1 F:
(SEQ ID NO: 9)
AGT ATA GGA ACT TCG AAG CAG CTC CAG CCT ACA AAT
AAA AAT GCC AGC CGA TCG GGC TGG

3' CDX Pho R:
(SEQ ID NO: 10)
TCA TTC AAT ACC TCT GTA AGT CGC ACA TAG AGT AAG
TTT CTG GTG GCG CAT TAT ACC AGC

The PCR protocol used:

| Template (10 ng/μl) | 1 μl |
|---|---|
| 5x HT PHUSION ® Buffer | 10 μl |
| 10 mM dNTPs | 1 μl |
| DMSO | 2 μl |
| Forward Oligo 20 μM | 1 μl |
| Reverse Oligo 20 μM | 1 μl |
| PHUSION ® Polymerase (2 U/μl) | 0.5 μl |
| H₂O | 33.5 μl |
| Total volume: | 50 μl |

The PCR conditions utilized were 1 cycle of 98° C. for 2 minutes, followed by 30 cycles of 98° C. for 10 seconds, 60° C. for 15 seconds, and 72° C. for 20 seconds, followed by a final cycle of 72° C. for 2 minutes.

In the second step, the kanamycin cassette was PCR amplified from pKD13 plasmid using the following primers. The forward oligo (5' Kan F) (SEQ ID NO:11) contains 35 bases of homology to sequence upstream of the integration site and the Reverse oligo (3' Kan R) (SEQ ID NO:12) contains 35 bases of homology to the 5' sequence of Pho1. The expected PCR product was 1380 base pairs in length.

5' Kan F:
(SEQ ID NO: 11)
AGG CGG TGG CTC GAT CTT AGC GAT GTG TGT AAG GCT
GCG CAT TCC GGG GAT CCG TCG ACC

3' Kan R:
(SEQ ID NO: 12)
AAA GGC AAA AAT GCC AGC CCG ATC GGC TGG CAT TTT
TAT TTG TAG CTG GAG CTG CTG TCG

The PCR protocol utilized:

| Template (10 ng/μl) | 1 μl |
|---|---|
| 5x HF PHUSION ® Buffer | 10 μl |
| 10 mM dNTPs | 1 μl |
| DMSO | 2 μl |
| Forward Oligo 20 μM | 1 μl |
| Reverse Oligo 20 μM | 1 μl |
| PHUSION ® Polymerase (2 U/μl) | 0.5 μl |
| H₂O | 33.5 μl |
| Total volume: | 50 μl |

The PCR conditions utilized were 1 cycle of 98° C. for 2 minutes, followed by 30 cycles of 98° C. for 10 seconds, 60° C. for 15 seconds and 72° C. for 45 seconds, followed by a final cycle of 72° C. for 2 minutes.

In step 3, both PCR products from the previous two steps were gel purified and used as template to assemble the final integration cassette using the following oligos in splice overlap and extension PCR (SOE). The final cassette was 1650 base pairs in length.

5' Kan F:
(SEQ ID NO: 11)
AGG CGG TGG CTC GAT CTT AGC GAT GTG TGT AAG GCT
GCG CAT TCC GGG GAT CCG TCG ACC

3' CDX Pho R:
(SEQ ID NO: 10)
TCA TTC AAT ACC TCT GTA AGT CGC ACA TAG AGT AAG
TTT CTG GTG GCG CAT TAT ACC AGC

The PCR protocol utilized:

| Template (10 ng of each PCR product) | 1 μl |
|---|---|
| 5x HF PHUSION ® Buffer | 10 μl |
| 10 mM dNTPs | 1 μl |
| DMSO | 2 μl |
| Forward Oligo 20 μM | 1 μl |
| Reverse Oligo 20 μM | 1 μl |
| PHUSION ® Polymerase (2 U/μl) | 0.5 μl |
| H₂O | 33.5 μl |
| Total volume: | 50 μl |

The PCR conditions utilized were 1 cycle of 98° C. for 2 minutes, followed by 30 cycles of 98° C. for 10 seconds, 65° C. for 15 seconds, and 72° C. for 1 minute, followed by a final cycle of 72° C. for 2 minutes. After this reaction, the PCR product was purified and desalted through a PCR purification column (Qiagen) and eluted with water.

The DNA sequence of the final cassette is shown below. The regions of homology with the chromosome are shown in bold:

(SEQ ID NO: 13)
AGGCGGTGGCTCGATCTTAGCGATGTGTGTAAGGCTGCGCATTCCGGGGA
TCCGTCGACCTGCAGTTCGAAGTTCCTATTCTCTAGAAAGTATAGGAACT
TCAGAGCGCTTTTGAAGCTCACGCTGCCGCAAGCACTCAGGGCGCAAGGG
CTGCTAAAGGAAGCGGAACACGTAGAAAGCCAGTCCGCAGAAACGGTGCT
GACCCCGGATGAATGTCAGCTACTGGGCTATCTGGACAAGGGAAAACGCA
AGCGCAAAGAGAAAGCAGGTAGCTTGCAGTGGGCTTACATGGCGATAGCT
AGACTGGGCGGTTTTATGGACAGCAAGCGAACCGGAATTGCCAGCTGGGG
CGCCCTCTGGTAAGGTTGGGAAGCCCTGCAAAGTAAACTGGATGGCTTTC
TTGCCGCCAAGGATCTGATGGCGCAGGGGATCAAGATCTGATCAAGAGAC
AGGATGAGGATCGTTTCGCATGATTGAACAAGATGGATTGCACGCAGGTT
CTCCGGCCGCTTGGGTGGAGAGGCTATTCGGCTATGACTGGGCACAACAG
ACAATCGGCTGCTCTGATGCCGCCGTGTTCCGGCTGTCAGCGCAGGGGCG
CCCGGTTCTTTTTGTCAAGACCGACCTGTCCGGTGCCCTGAATGAACTGC
AGGACGAGGCAGCGCGGCTATCGTGGCTGGCCACGACGGGCGTTCCTTGC
GCAGCTGTGCTCGACGTTGTCACTGAAGCGGGAAGGGACTGGCTGCTATT
GGGCGAAGTGCCGGGGCAGGATCTCCTGTCATCTCACCTTGCTCCTGCCG
AGAAAGTATCCATCATGGCTGATGCAATGCGGCGGCTGCATACGCTTGAT
CCGGCTACCTGCCCATTCGACCACCAAGCGAAACATCGCATCGAGCGAGC
ACGTACTCGGATGGAAGCCGGTCTTGTCGATCAGGATGATCTGGACGAAG
AGCATCAGGGGCTCGCGCCAGCCGAACTGTTCGCCAGGCTCAAGGCGCGC

-continued

```
ATGCCCGACGGCGAGGATCTCGTCGTGACCCATGGCGATGCCTGCTTGCC

GAATATCATGGTGGAAAATGGCCGCTTTTCTGGATTCATCGACTGTGGCC

GGCTGGGTGTGGCGGACCGCTATCAGGACATAGCGTTGGCTACCCGTGAT

ATTGCTGAAGAGCTTGGCGGCGAATGGGCTGACCGCTTCCTCGTGCTTTA

CGGTATCGCCGCTCCCGATTCGCAGCGCATCGCCTTCTATCGCCTTCTTG

ACGAGTTCTTCTAATAAGGGGATCTTGAAGTTCCTATTCCGAAGTTCCTA

TTCTCTAGAAAGTATAGGAACTTCGAAGCAGCTCCAGCCTACAAATAAAA

ATGCCAGCCGATCGGGCTGGCATTTTTGCCTTTAAATTGGTTTGACAGCT

TATCATCGACTGCACGGTGCACCAATGCTTCTGGCGTCAGGCAGCCATCG

GAAGCTGTGGTATGGCTGTGCAGGTCGTAAATCACTGCATAATTCGTGTC

GCTCAAGGCGCACTCCCGTTCTGGATAATGTTTTTTGCGCCGACATGTTT

GTGACAGATATATGACAGGAATTTGACAGATATATGACAGGCTGGTATAA

TGCGCCACCAGAAACTTACTCTATGTGCGACTTACAGAGGT
```

Example 3

Construction of a Strain with fabB Under Control of the Pho1 Promoter

This Example describes the construction of an *E. coli* strain with fabB under control of the Pho1 promoter. In this construct, the cassette described in Example 2 was used to replace the native regulatory region of the FabB gene in the chromosome of the *E. coli* strain W3110K (CGSC), as described below.

First, recombinase-induced cells were prepared. A single colony of strain W3110K containing plasmid pSIM5 (See, Datta et al., Gene 379:109-115 [2006]) was used to inoculate a 3 ml of LB media (Difco)+30 μg/mL chloramphenicol and cultivated overnight) at 30° C. 350 μL of this overnight culture were added to 40 ml of TB media (Difco)+30 μg/mL chloramphenicol (pre-warmed to 30° C.) in a 250 ml baffled Erlenmeyer flask. The cells were grown at 30° C. with shaking at 250 rpm for 2 hours and 45 minutes (~OD600 of 0.5). The flask was immediately transferred to a 42° C. water bath, and incubated with shaking at 300 rpm for 12 minutes (this step ensures that the recombinase has been induced). Immediately after induction, the culture was rapidly chilled in ice-water and left on ice for 5-10 min. The induced culture was transferred to a pre-chilled centrifuge tube and centrifuged for 10 min at ~4000×g at 4° C. The supernatant was aspirated and 1 ml of ice-cold sterile distilled H$_2$O was added to the cell pellet to resuspend the cells after which, another 40 ml of ice-cold distilled H$_2$O was added. The tube was centrifuged again as in the previous step (i.e., 10 min at ~4000×g at 4° C.). The resulting 40 ml supernatant was decanted and the pellet was resuspended in 1 ml ice-cold distilled H$_2$O. The cells were transferred to a pre-chilled microcentrifuge tube and centrifuged for 1 min at ~10,000×g in a 4° C. refrigerated microcentrifuge. The supernatant was aspirated and the wash step was repeated one more time. The resulting cell pellet was resuspended in ~250 μl of sterile ice-cold distilled H$_2$O and kept on ice until used.

Then, electrotransformation of linear PCR product into the recombinase-induced cells was performed by pipetting 1 to 10 μl (~100 ng) of salt-free PCR fragment into 50 μl of electrocompetent cells prepared in step 1. The cells and DNA mixture were transferred to a 1 mm cuvette on ice and electroporated at 1.7 kV. Immediately after electrotransformation, the cells were resuspended in 2 mL of SOC media (Invitrogen) in a new, sterile culture tube. The tubes were then incubated at 37° C. for ~3 hours to allow completion of recombination and expression of the drug-resistance gene.

Following incubation, the cells were selected for positive integrants. In this process, 100 μl of the culture obtained after the ~3 hours incubation described above, was plated onto agar plates with 20 g/mL kanamycin. Additionally, 1 mL of cells were spun down, resuspended in 100 μl of LB and plated on LA (Difco) plates with 40 μg/mL kanamycin. The plates were incubated at 37° C. overnight. Approximately ~20 colonies per 100 μl of culture were observed.

Following incubation, confirmation of the proper genomic modification was conducted. In this step, colonies from the above plates were streaked out onto non-selective LB plates to produce single colonies. Twelve (12) colonies from the non-selective plates were verified by PCR and sequencing. Two synthetic oligos were used to amplify the fabB regulatory region (FB genome-up and FB genome-down, as shown below). These oligos are located approximately 250 bases upstream or downstream of the modified region in the chromosome. The expected size of this PCR product was 3227 bp.

```
FB genome-up:
                                 (SEQ ID NO: 14)
TTG GAA AAA TAG ACA TCG TCA AAA TCT C FB genome-down:
                                 (SEQ ID NO: 15)
TGC AGC GCA AGG CGA GGA GTA TCC CCG TCT
```

The PCR protocol utilized:

| | |
|---|---|
| Template (colony dissolved in H2O) | 1 μl |
| 5x HERCULASE ® II Reaction Buffer | 10 μl |
| 10 mM dNTPs | 1 μl |
| Betaine 5M | 10 μl |
| Forward Oligo 20 μM | 1 μl |
| Reverse Oligo 20 μM | 1 μl |
| HERCULASE ® II Fusion DNA Polymerase (2 U/μl) | 0.5 μl |
| H$_2$O | 25.5 μl |
| Total volume: | 50 μl |

The PCR conditions utilized were 1 cycle of 95° C. for 2 minutes, followed by 30 cycles of 95° C. for 20 seconds, 60° C. for 30 seconds, and 72° C. for 3 minutes, followed by a final cycle of 72° C. for 2 minutes.

The obtained PCR products were fully sequenced using the following primers:

```
Kan 5' F1:
                                 (SEQ ID NO: 16)
ATT CCG GGG ATC CGT CGA CC

Kan 5' F2:
                                 (SEQ ID NO: 17)
GGC ACA ACA GAC AAT CGG CT

Kan 5' F3:
                                 (SEQ ID NO: 18)
CCT GCT TGC CGA ATA TCA TG

CDXPho Seq F1:
                                 (SEQ ID NO: 19)
GCC TTT AAA TTG GTT TGA CAG CT
```

-continued

FabB seqF1:
(SEQ ID NO: 20)
CGT GCA GTG ATT ACT GGC CTG

FabB seqF2:
(SEQ ID NO: 21)
ATG TGG TCA CCA AAG CGA TG

FabB seqF3:
(SEQ ID NO: 22)
GGT ACT TCG ACT CCG GTT GG

FabB seqF4:
(SEQ ID NO: 23)
CTG GTA ATG CGC AAG CTG AA

FabB seqR1:
(SEQ ID NO: 24)
AAT GCC CAG GCC AGT AAT C

CdxPho1 seq R1:
(SEQ ID NO: 25)
TAT CTG TCA CAA ACA TGT CG

Example 4

FabB mRNA Analysis by qPCR

In this Example, experiments conducted using qPCR to quantify the levels of fabB mRNA produced by the strains produced in Example 3 are described. In these experiments, the materials included the RNeasy Mini Kit (Qiagen), RNAprotect Bacterial Reagent (Qiagen), mercaptoethanol, ethanol, lysozyme (Sigma), proteinase K (Qiagen), RNAse-Free DNase Set (Qiagen), Zymo-RNA clean and concentrator-5 (Zymo), ImProm-II Reverse Transcription System (Promega), LightCycler 480 SYBR Green Master Mix (Roche), and qPCR primers.

In this protocol, RNA was prepared by adding a sample of culture directly to a tube with 2 volumes RNAprotect bacterial reagent. The contents were mixed and incubated at RT for 5 min. Typically, at an induction OD of ~0.5-0.8, an aliquot of approximately 1-1.5 mL was taken and ~0.25-0.4 mL were sampled at later time points. Each sample was centrifuged for 10 min at 5000×g and the supernatant was decanted. At this point were frozen at −80 or used directly in the RNeasy Mini Kit.

First, the RNA was prepared as directed in Protocol 4 of the RNeasy manual (enzymatic lysis and proteinase K digestion of bacteria). The RNA was quantitated using a Nanodrop 2000 instrument (Thermo). Next, the DNase 1 stock solution was prepared by dissolving the solid powder in 550 uL water by gentle mixing and distributed into 50 uL aliquots which were stored at −20° C. until use. The DNase reaction utilized ≤5 ug RNA, 3 uL RDD buffer, 1 uL DNase 1, and sufficient water to provide 30 uL of solution. The solution was incubated at 37° C. for 30 min. An additional 1 uL DNase was then added and the solution was incubated for another 30 min. An additional 1 ul DNase was added and the solution was incubated for 1 hour. The reactions were cleaned up using Zymo-RNA clean and concentrator-5, per the manufacturer's instructions and then eluted in 20 uL water. The RNA was quantified using a Nanodrop 2000 instrument (Thermo) and the final concentrations were adjusted to 25 ng/ul.

Next, cDNA was synthesized for use in qPCR using the Improm-II Reverse Transcription Kit™ (Promega). In this procedure, the RNA was primed using random hexamers (0.5 ul) provided in the kit, 10 mM dNTP (0.5 ul), and 4 uL of purified RNA (at 25 ng/ul). The mixture was heated at 70° C. for 5 min., and then quick chilled on ice for 2-3 min. Then, 5 ul of RT or no RT mix was added (at least one no RT control was run, in order to check for DNA contamination). The reverse transcriptase (RT) reaction was performed using 5× RT buffer (2.2 ul), 25 mM $MgCl_2$ (2.2 ul), RNAsin (0.25 ul), water (0.25 ul), and RT (0.5 ul), in a final volume of 5 ul. The mixture was incubated at 25° C. for 5 min, 42° C. for 1 hr, 70° C. for 15 min. After this, reactions were kept at 40 until they were used for qPCR reactions. Next, the cDNA was diluted 1:20 by adding 95 ul water to the 5 ul RT reaction. The qPCR reactions were run in triplicate, using appropriate controls (e.g., at least one no RT reaction and a no template control for each gene tested). The folA and the cysG genes were used as standards for normalization.

The primers sets used were:

DRFR (folA) (endogenous control)
(SEQ ID NO: 26)
DHFR-F TCTGACGCATATCGACGCAGAAGT (SEQ ID NO: 27)
DHFR-R GCCGCTCCAGAATCTCAAAGCAAT CysG (alternative endogenous control)
(SEQ ID NO: 28)
CysG-F TTGTCGGCGGTGGTGATGTCA (SEQ ID NO: 29)
CysG-R ATGCGGTGAACTGTGGAATAA FabB
(SEQ ID NO: 30)
FabB3F-ATCTCTGCGTGAAGGACGCGTT (SEQ ID NO: 31)
FabB3R-ATGAGGCCAGTGGTATCCAG The qPCR reaction mix contained 2×SYBR Master Mix, Roche (10 ul), water (5 ul), 10 uM forward primer (0.5 ul), 10 uM reverse primer (0.5 ul), and cDNA (1:20) (4 ul), to a final volume of 20 ul.

A LightCycler model 480 (Roche) with a 96-well plate was used to carry out the qPCR reactions. Reactions were run at 95° C. for 5 min, followed by 45 cycles of 95° C. for 10 seconds, 60° C. for 10 seconds, and 72° C. for 10 seconds. The melting curve was determined using 95° C. for 5 seconds, followed by 65° C. for 1 min, and a ramp to 95° C. For relative expression analysis, the relative quantitation, 2nd derivative max was used on the Roche480 to determine Cp values. To calculate relative mRNA from Cp values, the efficiency-corrected delta Ct method as described by Bookout et al. was used (See, Bookout et al., "High Throughput Real-Time Quantitative Reverse Transcription PCR," in *Current Protocols in Molecular Biology*, John Wiley and Sons Inc., Hoboken, N.J., pp., 15.8.1-15.8.28 [2006]).

Example 5

FabB Protein Quantification

In this Example, experiments conducted to quantify the relative amounts of the protein FabB in samples were conducted. In particular, specific peptides of FabB were identified and quantified by LC/MS, using the protocol described below.

Sample Collection:

First, 15 ml aliquots were collected at different time points. In the first step, fatty alcohols produced by the strains were first removed by extracting them by a dodecane wash using 3× dodecane (Sigma) per sample volume, vortexed, and the centrifuged for 10 min at 4000 rpm, 4° C. The supernatants were discarded and the cell pellets were washed with M9YE (without glucose) to wash away residual dodecane. The pellets were stored at −80° C. until further processing.

Cell Lysis:

To lyse the cell pellets, they were thawed on ice, then resuspended in lysis buffer (50 mM Tris pH 8.2, 75 mM NaCl, 8M Urea, containing cOmplete Mini EDTA-free protease inhibitor cocktail (Roche) (1 tablet/10 ml buffer). This buffer also contained 125 U/ml of Benzonase (EMD). Suspensions were sonicated on ice for 30 sec, and 90 sec chill (repeated 3 times). After lysis, the total protein concentrations were determined using the BCS assay following manufacturer recommendations (AMRESCO). The lysates were stored in −80° C. until further use.

In-Solution Digestion:

First, 500 μg of total protein was denatured in the presence of 5 μg of BSA and 5 μg ProteaseMAX surfactant (Promega) in a hot water bath sonicator for an hour, after which the samples were reduced with 5 mM TCEP (Sigma) for 60 minutes at 60° C. followed by alkylation with 15 mM iodoacetic acid (Sigma). This step was done in the dark, at room temperature, for 30 min. Fully denatured, alkylated, and reduced samples were transferred to 10 kDa spin filter columns (Sigma) and twice subjected to 50 mM Tris pH 8.5 buffer exchange. Trypsin was added in a 1:50 enzyme: substrate ratio (on the spin column). Samples were incubated at 37° C. overnight. Peptides were recovered by centrifuging at 15,000 RPM for 15 min. The collected peptides were diluted with 0.1% formic acid solution prior to LC-MS analysis.

LC-MS:

For each LC-MS analysis, 10 μL of sample is loaded onto a Michrom Magic C18 column (3μ, 100 Å, 0.2×50 mm) (Michrom). Peptides were detected on the mass spectrometer as they eluted off the column via an MRM method which consisted of tracking transitions as known in the art. Peak areas for each peptide are extracted, and subsequently summed, if they corresponded to the same protein. The amounts of each protein were determined based on normalization of peak areas with respect to spiked BSA.

The sequence of the peptides (and their positions in the protein sequence) identified and used for fabB quantification are shown below:

```
BSA (GenBank No. P02769):
                                        (SEQ ID NO: 32)
HLVDEPQNLIK (402-412)

(SEQ ID NO: 33)
LGEYGFQNALIVR (421-433)

(SEQ ID NO: 34)
LFTFHADICTLPDTEK (529-544)

(SEQ ID NO: 35)
RPCFSALTPDETYVPK (508-523)

E. coli FabB (GenBank No. P0A953)
                                        (SEQ ID NO: 36)
VGLIAGSGGGSPR (99-111)

(SEQ ID NO: 37)
LDTTGLIDR (54-62)

(SEQ ID NO: 38)
AVGPYVVTK (128-136)
```

```
                                        (SEQ ID NO: 39)
SGITFSQELK (31-40)

(SEQ ID NO: 40)
FQVFGADAMR (112-121)
```

Example 6

Shake Flask Protocol

Most of the commonly used growth media to cultivate *E. coli* (e.g., M9 and M63), contain excess phosphate, due to the fact that phosphate serves as a buffer in these media. Because of this, to evaluate a phosphate-repressible promoter, a medium containing low phosphate concentration (PMM2) was developed for shake-flask cultures. The composition of this media is shown below:

| Component | Final Concentration |
|---|---|
| $(NH_4)_2SO_4$ | 6 g/L |
| $KH_2PO_4$ | 0.2 g/L |
| $MgSO_4$ | 10 mM |
| Iron (III) citrate | 0.1 g/L |
| Thiamine | 4.5 mg/L |
| Trace elements | 1x |
| Glucose | 40 g/L |

Strains to be evaluated were first inoculated into 5 ml of 2YT media (16 g/L Bacto tryptone (Difco), 10 g/L Bacto yeast extract (Difco) and 5 g/L NaCL (Sigma), pH 7.0) and grown overnight at 30° C. in a shaker (one inch throw) at 250 rpm. After overnight growth, 2.5 ml were transferred into 50 ml of PMM2 media in 250 ml baffled shake flask (VWR) placed in a shaker at 250 rpm (two inch throw), at 30° C. After three hours of growth, IPTG (1 mM final concentration) was added to induce expression of the FAR enzyme (See, Example 7, below). Then, 280 μl aliquots were removed from each flask (for each strain being evaluated) at specific time points during the course of the experiment (0-72 hrs). Next, 250 ul were transferred to a deep-well plate (VWR) and 1 mL of methyl isobutyl ketone (Sigma) was added to each well and the plate was shaken vigorously (setting at 10 for a desktop plate shaker) for at least 2.5 hrs. The plate was centrifuged at 4000 rpm and 4° C. for 10 min. Then, 200 μl per well was transferred to a 96-well round bottom plate and analyzed via GC-FID to determine the amount and ratio of fatty alcohols produced.

Example 7

Evaluation of fabB Under Control of Pho1 in Shake-Flasks

In this Example, experiments conducted to provide an initial evaluation of the repression of fabB gene expression, under low phosphate conditions are described. In these experiments, the shake flask protocol described in Example 6 was used. The fabB gene was used to illustrate the utility of the present invention. It is not intended that the present invention be limited to expression of any particular gene, as modification(s) in the expression of any suitable gene finds use in the present invention. Plasmid pCDX11-8087 was produced as described in PCT/US12/69553. The sequence of this plasmid is provided below:

(SEQ ID NO: 41)

```
GGCATCCGCTTACAGACAAGCTGTGACCGTCTCCGGGAGCTGCATGTGTCAGAGGTTTTC
ACCGTCATCACCGAAACGCGCGAGGCAGCAGATCAATTCGCGCGCGAAGGCGAAGCGGC
ATGCATTTACGTTGACACCATCGAATGGTGCAAAACCTTTCGCGGTATGGCATGATAGCG
CCCGGAAGAGAGTCAATTCAGGGTGGTGAATGTGAAACCAGTAACGTTATACGATGTCG
CAGAGTATGCCGGTGTCTCTTATCAGACCGTTTCCCGCGTGGTGAACCAGGCCAGCCACG
TTTCTGCGAAAACGCGGGAAAAAGTGGAAGCGGCGATGGCGGAGCTGAATTACATTCCC
AACCGCGTGGCACAACAACTGGCGGGCAAACAGTCGTTGCTGATTGGCGTTGCCACCTC
CAGTCTGGCCCTGCACGCGCCGTCGCAAATTGTCGCGGCGATTAAATCTCGCGCCGATCA
ACTGGGTGCCAGCGTGGTGGTGTCGATGGTAGAACGAAGCGGCGTCGAAGCCTGTAAAG
CGGCGGTGCACAATCTTCTCGCGCAACGCGTCAGTGGGCTGATCATTAACTATCCGCTGG
ATGACCAGGATGCCATTGCTGTGGAAGCTGCCTGCACTAATGTTCCGGCGTTATTTCTTG
ATGTCTCTGACCAGACACCCATCAACAGTATTATTTTCTCCCATGAAGACGGTACGCGAC
TGGGCGTGGAGCATCTGGTCGCATTGGGTCACCAGCAAATCGCGCTGTTAGCGGGC CCAT
TAAGTTCTGTCTCGGCGCGTCTGCGTCTGGCTGGCTGGCATAAATATCTCACTCGCAATC
AAATTCAGCCGATAGCGGAACGGGAAGGCGACTGGAGTGCCATGTCCGGTTTTCAACAA
ACCATGCAAATGCTGAATGAGGGCATCGTTCCCACTGCGATGCTGGTTGCCAACGATCAG
ATGGCGCTGGGCGCAATGCGCGCCATTACCGAGTCCGGGCTGCGCGTTGGTGCGGATAT
CTCGGTAGTGGGATACGACGATACCGAAGACAGCTCATGTTATATCCCGCCGTTAACCAC
CATCAAACAGGATTTTCGCCTGCTGGGGCAAACCAGCGTGGACCGCTTGCTGCAACTCTC
TCAGGGCCAGGCGGTGAAGGGCAATCAGCTGTTGCCCGTCTCACTGGTGAAAAGAAAAA
CCACCCTGGCGCCCAATACGCAAACCGCCTCTCCCCGCGCGTTGGCCGATTCATTAATGC
AGCTGGCACGACAGGTTTCCCGACTGGAAAGCGGGCAGTAATAATTTAAATTGGTTTGA
CAGCTTATCATCGACTGCACGGTGCACCAATGCTTCTGGCGTCAGGCAGCCATCGGAAGC
TGTGGTATGGCTGTGCAGGTCGTAAATCACTGCATAATTCGTGTCGCTCAAGGCGCACTC
CCGTTCTGGATAATGTTTTTTGCGCCGACATAATTGTGAGCGCTCACAATTTCTGAAATG
AGCTGTTGACAATTAATCATCCGGCTCGTATAATGTGTGGAATTGTGAGCGGATAACAAT
TTCACACAGGAAACAGCGCCGCTGAGAAAAAGCGAAGCGGCACTGCTCTTTAACAATTT
ATCAGACAATCTGTGTGGGCACTCGACCGGAATTATCGATTAACTTTATTATTAAAAATT
AAAGGAGGAATAAACCATGGCGACTCAACAACAGAACAACGGTGCATCTGCATCCGGCG
TCTTGGAAATTCTTCGTGGAAAGCACGTTCTTATCACAGGTACTACCGGATTTTTGGGCA
AAGTGGTTCTGGAAAAGTTGATTCGTACTGTTCCGGATATTGGAGGTATTCATCTGCTGA
TTCGTGGCAATAAACGTCATCCAGCCGCTCGCGAACGTTTCCTGAACGAAATTGCGTCCT
CCTCCGTCTTCGAACGTTTGCGTCACGATGATAATGAAGCCTTCGAGACCTTCTTGGAAG
AACGTGTTCACTGTATTACCGGTGAGATTACTGAATCCCGTTTTGGTTTGACACCTGAGC
GTTTTCGTGCTTTGGCCGGTCAGGTTGACGCTTTTATTCATAGCGCTGCAAGCGTGAACTT
TCGTGAGCAATTGGATAAAGCCCTGAAAATCAACACCTTGTGTCTTGAAAATGTTGCTGC
TCTTGCAGAATTGAACTCCGCTATGGCGGTCATTCAGGTTTCCACTTGTTACGTTAACGGT
AAAACCTCCGGTCAAATTACCGAATCCGTCATTAAATCGGTGGCGAATCCATTCCCCGT
TCCACTGACGGTTACTACGAGATCGAAGAATTGGTCCATCTGTTGCAAGACAAGATTTCC
GATGTTAAAGCTCGTTACTCCGGCCGTGTTATGGGGAAAAAATTGGTTGATTTGGGTATT
```

-continued

```
CGTGAGGCCAATAATTACGGATGGTCCGACACCTACACATTCACCAAATGGTTGGGTGA

ACAACTGCTGATGAAGGCCTTGTCTGGTCGTTCTTTGACTATTGTGCGTCCCTCTATTATT

GAGTCCGCTTTGGAAGAACCTTCCCCTGGTTGGATCGAAGGCGTTAAAGTTGCCGATGCC

ATTATCTTGGCTTATGCCCGTGAAAAAGTTAGCCTGTTCCCTGGAAAACGTTCCGGCATT

ATTGATGTTATTCCTGTCGATTTGGTTGCGAACTCCATCATCTTGTCTCTGGCTGAGGCGT

TGTCTGGTTCTGGTCAACGTCGTATTTATCAATGTTGCAGCGGTGGTTCTAATCCAATCTC

CCTGGGTAAGTTCATTGATTATTTGAACGCCGAGGCTAAGACCAACTATGCTGCCTACGA

TCAACTGTTTTATCGTCGTCCTACTAAACCTTTCGTCGCCGTGAACCGTAAATTGTTTGAC

GTTGTTGTTGGTGTCATGCGTGTTGTCCTTTCTATTGCCCGCAAAGCTATGCGTTTGGCTG

GTGTAAATCGTGAGTTGAAAGTGCTTAAGAACCTTGATACGACCCGTAAACTTGCAACCA

TTTTTGGCTTCTATACTGCTCCCGACTATATCTTCCGTAACGATAGCTTGATGGCCCTGGC

TCAGCGTATGGGTGAATTGGATCGTGTTCTTTTCCCAGTTGATGCTCGTCAAATTGATTGG

CAGTTGTACTTGTGTAAAATTCATTTGCGTGGTCTGAACCGTTACGCTTTGAAGGAACGT

AAACTGTATTCTTCGCGTGCTGCTGATACTGACGATAAAACCGCCTAAGTCGACATAGAT

CTAGAACTTACTCGGAAGCTTCTTAATTAAGAGGATCCATTGACGTCTATGAATTCGTTT

AAACGGTCTCCAGCTTGGCTGTTTTGGCGGATGAGAGAAGATTTTCAGCCTGATACAGAT

TAAATCAGAACGCAGAAGCGGTCTGATAAAACAGAATTTGCCTGGCGGCAGTAGCGCGG

TGGTCCCACCTGACCCCATGCCGAACTCAGAAGTGAAACGCCGTAGCGCCGATGGTAGT

GTGGGGTCTCCCCATGCGAGAGTAGGGAACTGCCAGGCATCAAATAAAACGAAAGGCTC

AGTCGAAAGACTGGGCCTTTCGTTTTATCTGTTGTTTGTCGGTGAACGCTCTCCTGAGGCG

CCTGATGCGGTATTTTCTCCTTACGCATCTGTGCGGTATTTCACACCGCATATGGTGCACT

CTCAGTACAATCTGCTCTGATGCCGCATAGTTAAGCCAGCCCCGACACCCGCCAACACCC

GCTGACGAGCTTAGTAAAGCCCTCGCTAGATTTTAATGCGGATGTTGCGATTACTTCGCC

AACTATTGCGATAACAAGAAAAAGCCAGCCTTTCATGATATATCTCCCAATTTGTGTAGG

GCTTATTATGCACGCTTAAAAATAATAAAAGCAGACTTGACCTGATAGTTTGGCTGTGAG

CAATTATGTGCTTAGTGCATCTAACGCTTGAGTTAAGCCGCGCCGCGAAGCGGCGTCGGC

TTGAACGAATTGTTAGACATTATTTGCCGACTACCTTGGTGATCTCGCCTTTCACGTAGTG

GACAAATTCTTCCAACTGATCTGCGCGCGAGGCCAAGCGATCTTCTTCTTGTCCAAGATA

AGCCTGTCTAGCTTCAAGTATGACGGGCTGATACTGGGCCGGCAGGCGCTCCATTGCCCA

GTCGGCAGCGACATCCTTCGGCGCGATTTTGCCGGTTACTGCGCTGTACCAAATGCGGGA

CAACGTAAGCACTACATTTCGCTCATCGCCAGCCCAGTCGGGCGGCGAGTTCCATAGCGT

TAAGGTTTCATTTAGCGCCTCAAATAGATCCTGTTCAGGAACCGGATCAAAGAGTTCCTC

CGCCGCTGGACCTACCAAGGCAACGCTATGTTCTCTTGCTTTTGTCAGCAAGATAGCCAG

ATCAATGTCGATCGTGGCTGGCTCGAAGATACCTGCAAGAATGTCATTGCGCTGCCATTC

TCCAAATTGCAGTTCGCGCTTAGCTGGATAACGCCACGGAATGATGTCGTCGTGCACAAC

AATGGTGACTTCTACAGCGCGGAGAATCTCGCTCTCTCCAGGGGAAGCCGAAGTTTCCAA

AAGGTCGTTGATCAAAGCTCGCCGCGTTGTTTCATCAAGCCTTACGGTCACCGTAACCAG

CAAATCAATATCACTGTGTGGCTTCAGGCCGCCATCCACTGCGGAGCCGTACAAATGTAC

GGCCAGCAACGTCGGTTCGAGATGGCGCTCGATGACGCCAACTACCTCTGATAGTTGAGT

CGATACTTCGGCGATCACCGCTTCCCTCATGATGTTTAACTTTGTTTTAGGGCGACTGCCC

TGCTGCGTAACATCGTTGCTGCTCCATAACATCAAACATCGACCCACGGCGTAACGCGCT
```

```
TGCTGCTTGGATGCCCGAGGCATAGACTGTACCCCAAAAAAACAGTCATAACAAGCCAT

GAAAACCGCCACTGCGCCGTTACCACCGCTGCGTTCGGTCAAGGTTCTGGACCAGTTGCG

TGAGCGCATACGCTACTTGCATTACAGCTTACGAACCGAACAGGCTTATGTCCACTGGGT

TCGTGCCTTCATCCGTTTCCACGGTGTGCGTCACCCGGCAACCTTGGGCAGCAGCGAAGT

CGAGGCATTTCTGTCCTGGCTGGCGAACGAGCGCAAGGTTTCGGTCTCCACGCATCGTCA

GGCATTGGCGGCCTTGCTGTTCTTCTACGGCAAGGTGCTGTGCACGGATCTGCCCTGGCT

TCAGGAGATCGGAAGACCTCGGCCGTCGCGGCGCTTGCCGGTGGTGCTGACCCCGGATG

AAGTGGTTCGCATCCTCGGTTTTCTGGAAGGCGAGCATCGTTTGTTCGCCCAGCTTCTGTA

TGGAACGGGCATGCGGATCAGTGAGGGTTTGCAACTGCGGGTCAAGGATCTGGATTTCG

ATCACGGCACGATCATCGTGCGGGAGGGCAAGGGCTCCAAGGATCGGGCCTTGATGTTA

CCCGAGAGCTTGGCACCCAGCCTGCGCGAGCAGGGGAATTAATTCCCACGGGTTTTGCTG

CCCGCAAACGGGCTGTTCTGGTGTTGCTAGTTTGTTATCAGAATCGCAGATCCGGCTTCA

GCCGGTTTGCCGGCTGAAAGCGCTATTTCTTCCAGAATTGCCATGATTTTTTCCCCACGGG

AGGCGTCACTGGCTCCCGTGTTGTCGGCAGCTTTGATTCGATAAGCAGCATCGCCTGTTT

CAGGCTGTCTATGTGTGACTGTTGAGCTGTAACAAGTTGTCTCAGGTGTTCAATTTCATGT

TCTAGTTGCTTTGTTTTACTGGTTTCACCTGTTCTATTAGGTGTTACATGCTGTTCATCTGT

TACATTGTCGATCTGTTCATGGTGAACAGCTTTGAATGCACCAAAAACTCGTAAAAGCTC

TGATGTATCTATCTTTTTTACACCGTTTTCATCTGTGCATATGGACAGTTTTCCCTTTGATA

TGTAACGGTGAACAGTTGTTCTACTTTTGTTTGTTAGTCTTGATGCTTCACTGATAGATAC

AAGAGCCATAAGAACCTCAGATCCTTCCGTATTTAGCCAGTATGTTCTCTAGTGTGGTTC

GTTGTTTTGCGTGAGCCATGAGAACGAACCATTGAGATCATACTTACTTTGCATGTCAC

TCAAAAATTTTGCCTCAAAACTGGTGAGCTGAATTTTTGCAGTTAAAGCATCGTGTAGTG

TTTTTCTTAGTCCGTTATGTAGGTAGGAATCTGATGTAATGGTTGTTGGTATTTTGTCACC

ATTCATTTTATCTGGTTGTTCTCAAGTTCGGTTACGAGATCCATTTGTCTATCTAGTTCA

ACTTGGAAAATCAACGTATCAGTCGGGCGGCCTCGCTTATCAACCACCAATTTCATATTG

CTGTAAGTGTTTAAATCTTTACTTATTGGTTTCAAAACCCATTGGTTAAGCCTTTTAAACT

CATGGTAGTTATTTTCAAGCATTAACATGAACTTAAATTCATCAAGGCTAATCTCTATATT

TGCCTTGTGAGTTTTCTTTTGTGTTAGTTCTTTTAATAACCACTCATAAATCCTCATAGAG

TATTTGTTTTCAAAAGACTTAACATGTTCCAGATTATATTTTATGAATTTTTTTAACTGGA

AAAGATAAGGCAATATCTCTTCACTAAAAACTAATTCTAATTTTTCGCTTGAGAACTTGG

CATAGTTTGTCCACTGGAAAATCTCAAAGCCTTTAACCAAAGGATTCCTGATTTCCACAG

TTCTCGTCATCAGCTCTCTGGTTGCTTTAGCTAATACACCATAAGCATTTTCCCTACTGAT

GTTCATCATCTGAGCGTATTGGTTATAAGTGAACGATACCGTCCGTTCTTTCCTTGTAGGG

TTTTCAATCGTGGGGTTGAGTAGTGCCACACAGCATAAAATTAGCTTGGTTTCATGCTCC

GTTAAGTCATAGCGACTAATCGCTAGTTCATTTGCTTTGAAAACAACTAATTCAGACATA

CATCTCAATTGGTCTAGGTGATTTTAATCACTATACCAATTGAGATGGGCTAGTCAATGA

TAATTACTAGTCCTTTTCCTTTGAGTTGTGGGTATCTGTAAATTCTGCTAGACCTTTGCTG

GAAAACTTGTAAATTCTGCTAGACCCTCTGTAAATTCCGCTAGACCTTTGTGTGTTTTTTT

TGTTTATATTCAAGTGGTTATAATTTATAGAATAAAGAAAGAATAAAAAAAGATAAAAA
```

```
GAATAGATCCCAGCCCTGTGTATAACTCACTACTTTAGTCAGTTCCGCAGTATTACAAAA

GGATGTCGCAAACGCTGTTTGCTCCTTCTACAAAACAGACCTTAAAACCCTAAAGGCTTAAG
```

The fabB gene is an *E. coli* gene encodes the FabB enzyme involved in fatty acid biosynthesis. FabB catalyzes the elongation of Acyl-ACPs to chain lengths up to 16 and 18 carbons, in particular unsaturated fatty acids which are essential for membrane formation. As direct readout of the total capacity of fatty acid biosynthesis in a cell, the fatty alcohol reductase (FAR) from *Marinobacter algicola* was used, as it is known to use Acyl-ACPs to produce fatty alcohols of different chain lengths (See e.g., U.S. Pat. No. 8,216,815). Reduction in FabB elongation capacity in cells where FAR is present, should have at least two effects: (1) a reduction in the total amount of fatty alcohols that the cells can produce; and (2) as the total activity of FabB decreases after the gene has been repressed, a reduction in the chain length of the fatty alcohols produced by FAR should occur. As shown in Table 7-1, after 42 h of incubation, the strain where fabB was being expressed from its native promoter, produced ~1.6 g/L of fatty alcohols and the percentage of C12:0 fatty alcohol was ~7%. The strain containing fabB under control of the Pho1 promoter produced only ~0.9 g/L of fatty alcohols, and ~47% of the fatty alcohols were C12:0, indicating that the cell's capability to elongate fatty acids was limited.

TABLE 7.1

Fatty Alcohol Production

| Strain | Total Fatty Alcohol Production (g/L) | % C12:0 Fatty Alcohols |
|---|---|---|
| W3110K/pCDX11-8087 | ~1.60 | ~7 |
| W3100K::Km-Pho1-fabB/pCDX11-8087 | ~0.9 | ~47 |

Example 8

Strain Evaluation in 10 L Fermentors

This Example describes experiments developed to collect large samples for mRNA and protein analysis. In these experiments, 10 L cultures were carried out using the conditions described below for each strain:

Strain W3110K/pCDX11-8087:

In an aerated, agitated stirred tank 10 L fermentor, 3 L of growth medium containing 33 g D-glucose monohydrate (Corn Products), 2.6 g ammonium sulfate (Sigma), 10 g Tastone yeast extract (Sensient), 9 g potassium phosphate dibasic anhydrous (Sigma), 3 g sodium citrate dihydrate (Mallinkrodt), 1 g ammonium iron (III) citrate (Alfa Aesar), 50 mg calcium chloride dehydrate (Sigma), 55 mg zinc sulfate heptahydrate (Sigma), 166 mg magnesium sulfate (J.T. Baker), 12.5 mg manganese sulfate heptahydrate (Sigma), 25 mg copper sulfate pentahydrate (Sigma), 2.5 mg ammonium molybdate tetrahydrate (Sigma), 0.5 mg sodium borate decahydrate (Sigma), 25 mg cobalt chloride hexahydrate (Sigma), 3 mL antifoam B (Sigma), and 300 mg spectinomycin (Calbiochem) were brought to a temperature of 30° C. The fermentor was inoculated with 80 mL of a late exponential culture of *E. coli*. The inoculum was grown in a 1000 mL baffled shake flask containing 100 mL of 10 g/L D-glucose (Sigma). 6 g/L sodium phosphate dibasic anhydrous (Mallinkrodt), 3 g/L potassium phosphate monobasic anhydrous (Mallinkrodt), 1 g/L ammonium chloride (BDH), 2 g/L Tastone yeast extract (Sensient), 0.5 g/L sodium chloride (Sigma), 100 mg/L spectinomycin (Calbiochem) at 30° C., 250 rpm until the OD600 reached 2-3. The fermentor was agitated at 300-1800 rpm and air supplied at 3 slpm to maintain a minimum dissolved oxygen level of 30% of saturation. The pH of the culture was controlled, to maintain it at 7.0 by addition of a solution containing 28-30% ammonia (Sigma) in the form of ammonium hydroxide.

After consumption of the 10 g/L initial glucose, an exponential fed-batch growth phase with a specific growth rate of 0.15 h$^{-1}$ (controlled by limiting glucose) was initiated by exponential addition of feed solution containing 715 g/L D-glucose monohydrate (Corn Products), 2 g/L magnesium sulfate to the fermentor. The exponential feed profile was maintained for 10 hours. The expression of the FAR variant was induced at the end of the exponential fed-batch growth phase by the addition of isopropyl-B-D-thiogalactoside (IPTG, Richman Chemical) to a final concentration of 1 mmol/L. Production of fatty alcohol was maintained by a pH-stat protocol using a feed solution containing 715 g/L D-glucose monohydrate (Corn Products), 2 g/L magnesium sulfate (Sigma). The addition of feed solution (60 g of glucose per 1 hour pulse) was triggered when pH spiked above 7.15. In parallel, a 50 g/L potassium phosphate monobasic (Sigma) solution was fed at a constant rate of 0.03 mL/min immediately after IPTG addition until the end of the fermentation. The production of fatty alcohols was maintained for an additional 68 hours at 30° C.

Strain W3110K::Km-Pho1-fabB/pCDX11-8087:

In an aerated, agitated stirred tank 10 L fermentor, 3 L of growth medium containing 29.7 g D-glucose monohydrate (Corn Products), 2.6 g ammonium sulfate (Sigma), 10 g Tastone yeast extract (Sensient), 1.28 g potassium phosphate dibasic anhydrous (Sigma), 3 g sodium citrate dihydrate (Mallinkrodt), 1 g ammonium iron (III) citrate (Alfa Aesar), 50 mg calcium chloride dehydrate (Sigma), 55 mg zinc sulfate heptahydrate (Sigma), 166 mg magnesium sulfate (J.T. Baker), 12.5 mg manganese sulfate heptahydrate (Sigma), 25 mg copper sulfate pentahydrate (Sigma), 2.5 mg ammonium molybdate tetrahydrate (Sigma), 0.5 mg sodium borate decahydrate (Sigma). 25 mg cobalt chloride hexahydrate (Sigma), 3 mL antifoam B (Sigma), and 300 mg spectinomycin (Calbiochem) were brought to a temperature of 30° C. The fermentor was inoculated with 80 mL of a late exponential culture of *E. coli*. The inoculum was grown in a 1000 mL baffled shake flask containing 100 mL of 10 g/L D-glucose (Sigma), 6 g/L sodium phosphate dibasic anhydrous (Mallinkrodt), 3 g/L potassium phosphate monobasic anhydrous (Mallinkrodt), 1 g/L ammonium chloride (BDH), 2 g/L Tastone yeast extract (Sensient), 0.5 g/L sodium chloride (Sigma), 100 mg/L spectinomycin (Calbiochem) at 30° C., 250 rpm until the OD600 reached 2-3. The fermentor was agitated at 300-1800 rpm and air supplied at 3 slpm to maintain a minimum dissolved oxygen level of 30% of saturation. The pH of the culture was controlled at 7.0 by addition of a solution containing 28-30% ammonia (Sigma) in the form of ammonium hydroxide.

After consumption of the 4.85 mmol/L initial phosphate (as 0.85 g/L potassium phosphate dibasic), an exponential fed-batch growth phase with a specific growth rate of 0.25 h (controlled by limiting phosphate) was initiated by exponential addition of feed solution containing 715 g/L D-glucose monohydrate (Corn Products), 27 g/L potassium phosphate monobasic, 2 g/L magnesium sulfate to the fermentor. The exponential feed profile was maintained for 8.2 hours, allowing 3 cell doubling events under phosphate limiting conditions. The expression of the FAR variant was induced at the end of the exponential fed-batch growth phase by the addition of isopropyl-B-D-thiogalactoside (IPTG, Richman Chemical) to a final concentration of 1 mmol/L. Production of fatty alcohol was maintained by a pH-stat protocol using a feed solution containing 715 g/L D-glucose monohydrate (Corn Products), 2 g/L magnesium sulfate (Sigma). The addition of feed solution (60 g of glucose per 1 hour pulse) was triggered when the pH spiked above 7.15. In parallel, a 50 g/L potassium phosphate monobasic (Sigma) solution was fed at a constant rate of 0.03 mL/min immediately after IPTG addition until the end of the fermentation. The production of fatty alcohols was maintained for another 68 hours at 30° C.

Example 9

Evaluation of fabB Gene Expression Under Control of the Pho1 Promoter in 10 L Fermentors This Example describes experiments conducted to determine the level of control of the Pho1 promoter in larger fermentors. The experiment described in Example 7 above, indicates that fabB under the Pho1 promoter was repressed by low phosphate conditions. To better control the onset of phosphate limitation and collect larger samples to quantify fabB mRNA and FabB protein, 10 L fermentations were carried out according to the procedures described in Example 8 above using the strains described in Example 7.

Samples were taken at different time points and were used to quantify the relative amount of FabB-specific peptides as described in Example 5 and fabB mRNA relative abundance as described in Example 4. After analysis, the relative amounts of FabB protein or fabB mRNA measured at the onset of the phosphate limitation (12 hours of fermentation) was considered to be 100% and was used to calculate the percentage of FabB protein and fabB mRNA in the samples taken at 24 hours (i.e., 12 hours after phosphate limitation started). These results are shown in Table 9-1.

TABLE 9.1

Relative Concentration of FabB Protein and mRNA After 12 Hours Under Phosphate-Limiting Conditions

| Strain | Relative FabB Protein Concentration | Relative fabB mRNA Concentration |
|---|---|---|
| W3110K/pCDX11-8087 | 87% | 42% |
| W3100K::Km-Pho1-fabB/pCDX11-8087 | 18% | ~1% |

As shown in Table 9-1, at 12 hours after phosphate limitation started, both the FabB protein and fabB mRNA were significantly lower in the strain where fabB was under control of the Pho1 promoter.

Example 10

Construction of the Promoter Pho17

As indicated in Example 1, the Pho1 promoter was designed to obtain high levels of expression by using the consensus sequences for the −35 and −10 regions. In some applications, strong promoters are not needed to express a gene. Thus, in this Example, experiments conducted to design a weaker promoter where the −35 region, TTGACA was changed to GTGACA (1 bp change) are described. This new promoter is referred to herein as "Pho17." It is known that mutations in the −35 or −10 regions or in the DNA between these two regions (i.e., the spacer region), can affect drastically promoter strength (See e.g., Moyie et al., J. Bact., 173:1944-1950 [1991]; and U.S. Pat. No. 7,199,233). As shown in FIG. 1, another consequence of the Pho1 promoter design was that one of the PhoB boxes contained 1 bp that was different from the consensus. The 1 bp change in Pho17 created two PhoB consensus boxes (See, FIG. 1). Because of this, it was expected that the Pho17 promoter would be weaker than Pho1 and probably more repressible by PhoB~Pi.

The sequences in FIG. 1 are provided below:

Pho1:
(SEQ ID NO: 4)
GTGACAGATATATGACAGGAATTTGACAGATATATGACAGGCTGGTATAA

TGCGCCACCA

Pho17:
(SEQ ID NO: 5)
GTGACAGATATATGACAGGAATGTGACAGATATATGACAGGCTGGTATAA

TGCGCCACCA

Promoter Pho17 was constructed by mutagenesis of the Km-Pho1 cassette described in Example 2. For such a purpose, this cassette was converted first into a replicating plasmid by ligating it with the R6K origin of replication (R6Kori). The R6Kori was obtained by PCR using the R6KF1 and R6KR1 primers, and plasmid pKD32 obtained from the E. coli Stock Center as template.

R6KF1:
(SEQ ID NO: 42)
5' CTGTCAGCCGTTAAGTGTTCCTGTG

R6KR1:
(SEQ ID NO: 43)
5' CAGTTCAACCTGTTGATAGTACG

The PCR reaction contained:

| Template (10 ng/μl) | 2 μl |
|---|---|
| 5x HF PHUSION ® Buffer | 10 μl |
| 10 mM dNTPs | 1 μl |
| Oligo 50 μM | 0.5 μl |
| PHUSION ® Polymerase (2 U/μl) | 0.5 μl |
| Sterile H$_2$O | 36.5 μl |
| Total volume: | 50 μl |

The PCR conditions used were: 1 cycle of 98° C. for 30 seconds, followed by 25 cycles of 98° C. for 30 seconds and 60° C. for 30 seconds, seconds, followed by a final cycle of 72° C. for 2 minutes. This PCR product was purified and ligated to the cassette described in Example 2, using the Quick Ligation kit (New England BioLabs), following the manufacturer's protocol. Ligated products were transformed into PIR1 competent cells accordingly manufacturer recommended procedure (Invitrogen). After transformation, cells were plated on LA (Difco) plates containing 25 ug/ml Km. One colony from these plates was used to purify the plasmid Pho1-R6K.

Plasmid Pho1-R6K was used as template for mutagenesis using the QuikChange kit (Agilent). The oligo (PhoBboxT-toGF) was used to change the nucleotide at the 5' end of PhoB Box from T to G.

5' PhoBboxTtoGF:
(SEQ ID NO: 44)
ATATGACAGGAATGTGACAGA

The mutagenesis protocol was carried out as recommended by the supplier, except that in the last step. PIR1 cells were used to transform the mutated plasmid. A plasmid containing the proper modification was identified by sequencing and named pPho17-R6K.

The DNA sequence of the mutated cassette is shown below, with the primer sequence underlined and the modified base in bold within the underlined region.

(SEQ ID NO: 45)
AGGCGGTGGCTCGATCTTAGCGATGTGTGTAAGGCTGCGCATTCCGGGGA

TCCGTCGACCTGCAGTTCGAAGTTCCTATTCTCTAGAAAGTATAGGAACT

TCAGAGCGCTTTTGAAGCTCACGCTGCCGCAAGCACTCAGGGCGCAAGGG

CTGCTAAAGGAAGCGGAACACGTAGAAAGCCAGTCCGCAGAAACGGTGCT

GACCCCGGATGAATGTCAGCTACTGGGCTATCTGGACAAGGGAAAACGCA

AGCGCAAAGAGAAAGCAGGTAGCTTGCAGTGGGCTTACATGGCGATAGCT

AGACTGGGCGGTTTTATGGACAGCAAGCGAACCGGAATTGCCAGCTGGGG

CGCCCTCTGGTAAGGTTGGGAAGCCCTGCAAAGTAAACTGGATGGCTTTC

TTGCCGCCAAGGATCTGATGGCGCAGGGGATCAAGATCTGATCAAGAGAC

AGGATGAGGATCGTTTCGCATGATTGAACAAGATGGATTGCACGCAGGTT

CTCCGGCCGCTTGGGTGGAGAGGCTATTCGGCTATGACTGGGCACAACAG

ACAATCGGCTGCTCTGATGCCGCCGTGTTCCGGCTGTCAGCGCAGGGGCG

CCCGGTTCTTTTTGTCAAGACCGACCTGTCCGGTGCCCTGAATGAACTGC

AGGACGAGGCAGCGCGGCTATCGTGGCTGGCCACGACGGGCCGTTCCTTG

CGCAGCTGTGCTCGACGTTGTCACTGAAGCGGGAAGGGACTGGCTGCTAT

TGGGCGAAGTGCCGGGGCAGGATCTCCTGTCATCTCACCTTGCTCCTGCC

GAGAAAGTATCCATCATGGCTGATGCAATGCGGCGGCTGCATACGCTTGA

TCCGGCTACCTGCCCATTCGACCACCAAGCGAAACATCGCATCGAGCGAG

CACGTACTCGGATGGAAGCCGGTCTTGTCGATCAGGATGATCTGGACGAA

GAGCATCAGGGGCTCGCGCCAGCCGAACTGTTCGCCAGGCTCAAGGCGCG

CATGCCCGACGGCGAGGATCTCGTCGTGACCCATGGCGATGCCTGCTTGC

CGAATATCATGGTGGAAAATGGCCGCTTTTCTGGATTCATCGACTGTGGC

CGGCTGGGTGTGGCGGACCGCTATCAGGACATAGCGTTGGCTACCCGTGA

TATTGCTGAAGAGCTTGGCGGCGAATGGGCTGACCGCTTCCTCGTGCTTT

ACGGTATCGCCGCTCCCGATTCGCAGCGCATCGCCTTCTATCGCCTTCTT

GACGAGTTCTTCTAATAAGGGGATCTTGAAGTTCCTATTCCGAAGTTCCT

ATTCTCTAGAAAGTATAGGAACTTCGAAGCAGCTCCAGCCTACAAATAAA

AATGCCAGCCGATCGGGCTGGCATTTTTGCCTTTAAATTGGTTTGACAGC

TTATCATCGACTGCACGGTGCACCAATGCTTCTGGCGTCAGGCAGCCATC

-continued
GGAAGCTGTGGTATGGCTGTGCAGGTCGTAAATCACTGCATAATTCGTGT

CGCTCAAGGCGCACTCCCGTTCTGGATAATGTTTTTTGCGCCGACATGTT

TGTGACAGAT<u>ATATGACAGGAATGTGACAGATATATGA</u>CAGGCTGGTATA

ATGCGCCACCAGAAACTTACTCTATGTGCGACTTACAGAGGT

Example 11

Construction of W3110K-Δ4 Strain

Experiments conducted to construct the E. coli strain W3110K-D4 are described in this Example. This strain was designed to be suitable for large-scale fermentation processes. The following deletions were made to the starting E. coli W3110K (CGSC) strain: ΔfhuA; ΔldhA; ΔadhE and genes involved in colanic acid biosynthesis Δwza-wcaM. Each of the four deletions was carried out in a two-step process using lambda-RED technology known in the art (See, Datta et al., Gene 379:109-115 [2006]). In the first step, the gene(s) of interest was/were replaced with a dsDNA cassette encoding a kanamycin resistance marker (Km). In the second step, the Km marker was seamlessly removed from the genome using a ssDNA oligo using methods known in the art (See, Datta et al., supra). To exemplify this process, the deletion of the fhuA gene is described below.

For the deletion off fhuA, a dsDNA kanamycin resistance cassette was first PCR amplified from plasmid pKD13 (CGSC) using the following primers:

fhuA-deletion_F:
(SEQ ID NO: 46)
5'-ACGTTATCATTCACTTTACATCAGAGATATACCAATGGCGATTCCGGGGA
TCCGTCGACC-3' fhuA-deletion_R:
(SEQ ID NO: 47)
5'-AGAGAAATTAGAAACGGAAGGTTGCGGTTGCAACGACCTGTGTAGGCTGG
AGCTGCTTCG-3'

The PCR reaction was carried out using the enzyme PHUSION® DNA polymerase (New England BioLabs) with an initial denaturation step at 98° C. for 30 sec, followed by 30 cycles of the steps: 98° C. for 5 sec, 63° C. for 20 sec and 72° C. for 40 sec. This was followed by a final elongation step at 72° C. for 5 min. After the PCR reaction, the PCR product was purified through a PCR purification column (Qiagen) and eluted with water.

Strain W3110K was transformed with plasmid pSIM5 (Datta et al., supra). Homologous recombination-proficient electrocompetent cells were prepared as described by Datta et al., (supra), and were transformed with 500 ng of the kanamycin cassette from above. Cells were recovered at 32° C. for three hours, plated on LB agar plates containing 20 micrograms/ml of kanamycin, and incubated 24 hours at 32° C. A single colony was streaked onto a fresh LB agar plate with 30 micrograms/ml chloramphenicol (to maintain the pSIM5 plasmid) and a purified colony confirmed to have the fhuA gene replaced with the kanamycin cassette was named W3110K-ΔfhuA::Km.

Next, the kanamycin marker was removed from the above cells using homologous recombination with a ssDNA oligonucleotide. Homologous recombination proficient electrocompetent cells were prepared from strain W3110K-ΔfhuA::Km with the pSIM5 plasmid as described above and the cells were transformed with 500 ng of the oligonucleotide (fhuA(2-10)_del_oligo) shown below. In this sequence, the "*" indicates the presence of phosphorothioate bonds. This oligonucleotide contains four bases that were modified during synthesis of the oligonucleotide by the manufacturer (GenScript). It is known that these modifications make the oligonucleotide resistant to certain cellular nucleases.

fhuA(2-10)_del_oligo:
(SEQ ID NO: 48)
5'-A*G*A*G*AAATTAGAAACGGAAGGTTGCGGTTGCAACGACCTGCGCCAT TGGTATATCTCTGATGTAAAGTGAATGATAACGT-3'

Cells were recovered at 32° C. for five hours and dilutions were plated on LB agar plates and incubated 24 hours at 32° C. Petri plates with cell dilutions resulting in about 500 colonies/dish were replica plated onto fresh LB (Difco) and LA (Difco) plus kanamycin plates. A kanamycin sensitive colony was struck onto a fresh LA (Difco) plate with 30 micrograms/ml chloramphenicol (to maintain the pSIM5 plasmid) and a purified colony confirmed to have the correct, seamless deletion of the Km cassette, was named W3110K-ΔfhuA.

The subsequent deletions of the ldhA and adhE genes and all the genes of the region wza to wcaM were performed as described above for the fhuA gene. The primers for amplifying the dsDNA cassette from pKD13 and the oligos used for the seamless deletion of the markers, are shown below for each of the ldhA and adhE genes and the wza-wcaM genes:

ldhA-deletion_F:
(SEQ ID NO: 49)
5'-AGCTTAAATGTGATTCAACATCACTGGAGAAAGTCTTATGATTCCGGGGA TCCGTCGACC-3' ldhA-deletion_R:
(SEQ ID NO: 50)
5'-ATGCAGGGGAGCGGCAAGATTAAACCAGTTCGTTCGGGCATGTAGGCTGG AGCTGCTTCG-3' ldhA(1-6)_del_oligo:
(SEQ ID NO: 51)
5'-A*G*C*T*TAAATGTGATTCAACATCACTGGAGAAAGTCTTATGTGCCCG AACGAACTGGTTTAATCTTGCCGCTCCCCTGCAT-3'
(* = phosphorothioate bonds)

adhE-deletion_F:
(SEQ ID NO: 52)
5'-ATTTACTAAAAAAGTTTAACATTATCAGGAGAGCATTATGATTCCGGGGA TCCGTCGACC-3' adhE-deletion_R:
(SEQ ID NO: 53)
5'-TGCCAGACAGCGCTACTGATTAAGCGGATTTTTTCGCTTTTGTAGGCTGG AGCTGCTTCG-3' adhE(1-6)_del_oligo:
(SEQ ID NO: 54)
5'-A*T*T*T*ACTAAAAAAGTTTAACATTATCAGGAGAGCATTATGAAAGCG AAAAAATCCGCTTAATCAGTAGCGCTGTCTGGCA-3'
(* = phosphorothioate bonds)

wza-deletion_F:
(SEQ ID NO: 55)
5'-AGGATAATTACTCTGCCAAAGTGATAAATAAACAATGATGATTCCGGGGA TCCGTCGACC-3' wcaM-deletion_R:
(SEQ ID NO: 56)
5'-GCAATCTAAAGTTAATCTTCTCCACATTAACAATATGGTGTGTAGGCTGG AGCTGCTTCG-3' wza-wcaM(2-18)_del_oligo:
(SEQ ID NO: 57)
5'-G*C*A*A*TCTAAAGTTAATCTTCTCCACATTAACAATATGGTGCATCAT TGTTTATTTATCACTTTGGCAGAGTAATTATCCT-3'
(* = phosphorothioate bonds)

The final strain was confirmed by DNA sequencing to have seamless deletions of all four loci and was named "W3110K-Δ4" (W3110K-ΔfhuA-ΔldhA-ΔadhE-Δwza-wcaM).

Example 12

High Throughput Plate Assay

This Example describes the high throughput plate assays and media M9YE used in the development of the present invention. Medium M9YE has the following composition:

| | |
|---|---|
| Sodium phosphate dibasic (Sigma) | 6 g/L |
| Potassium phosphate monobasic (Sigma) | 3 g/L |
| Ammonium chloride (Sigma) | 1 g/l |
| Sodium chloride (Omnipur) | 0.5 g/L |
| Bis-Tris (Calbiochem) | 31.4 g/L |
| Tastone 154AG (Sensient) | 2 g/L |
| Glucose (Sigma) | 50 (or 10) g/L |
| pH adjusted to 7.0 with NaOH | |

A single E. coli colony was used to inoculate each well of a 96-well plate filled with 180 ul/well of M9YE media (with 1% glucose and a selection antibiotic). The plate was grown overnight (18-20 hrs) at 30° C., 85% relative humidity and shaking at 200 rpm. Once the cells reached saturation, 5% of the overnight growth was used to inoculate a 96-well plate filled with 380 ul/well of M9YE media containing 5% glucose and the selection antibiotic. The plate was placed in a shaker set to 250 rpm, 30° C. with a two inch throw. After two hours of growth. IPTG (1 mM final concentration) was added to induce the FAR enzyme. The deep-well plate containing the constructs remained in the shaker for ~72 hrs. 1 mL of methyl isobutyl ketone (MIBK) was added to each well, and the plate was shaken vigorously (setting at 10 for a desktop plate shaker) for at least 2.5 hrs. The plate was centrifuged at 4000 rpm at 4° C. for 10 min. 200 μl per well was transferred to a 96-well round bottom plate and analyzed via GC-FID to evaluate the fatty alcohol total titers and composition.

Example 13

Construction of Strains with fabA Under Control of the Pho1 or Pho17 Promoter

In this Example, experiments conducted to produce *E. coli* strains with the fabA gene under control of either the Pho1 or Pho17 promoter are described. The fabA gene is an essential *E. coli* which encodes an enzyme with two catalytic activities, namely a 3-hydroxyl-acyl-ACP dehydratase and a trans-Δ2-decenoyl-ACP to cis-Δ3-decenoyl-ACP isomerase activity. This isomerase function is essential for the biosynthesis of unsaturated fatty acids. To evaluate the activity of the Pho17 promoter, the Km-Pho17 cassette described in Example 10 was integrated in front of the fabA gene in the chromosome of strain W3110K-Δ4 strain (See, Example 11). As a control, the Km-Pho1 cassette (See, Example 2) was cloned in front of fabA in another strain. The Km-Pho1-fabA and Km-Pho17-fabA cassettes were generated by PCR using the pPho1-R6K or pPho17-R6K plasmids (described in Example 10), with primers FabAPhoR and ycgKanF.

ycgKanF:
(SEQ ID NO: 58)
GGCCATTACGTTGGCTGAACTGGTTTATTCCGAACTGATCATTCCGGGGA

TCCGTCGACC

FabAPhoR:
(SEQ ID NO: 59)
GTTTATCTACCATGTTCTCTGTAAGCCTTATTTTATTGAAGTGGTGGCGC

ATTATACCAGC

The PCR conditions to generate these cassettes were as described in step 3 of Example 2. These cassettes were integrated in the chromosome of strain W3110K-Δ4 strain (See, Example 11) using the protocol described in Example 3. Confirmation of the proper genomic modifications was obtained by PCR (See, Example 3) using the following primers:

ycbzckF:
(SEQ ID NO: 60)
TGGCGAAGGCCAAACGACGC fabAseqR:
(SEQ ID NO: 61)
TCATCAGCATGTTCGGTGCTGGC Example 14

Evaluation of Strains Containing fabA Under Control of the Pho1 or Pho17 Promoter This Example describes experiments to evaluate strains containing fabA under control of either the Pho1 or Pho17 promoter. The strains described in Example 13 were grown according to the plate protocol described in Example 12, and total fatty alcohol (FOH) concentrations and saturation levels were analyzed. As shown in Table 14-1 below, the strains with fabA under control of its native promoter or the Pho1 promoter produced the same amount of fatty alcohols, with very similar saturation levels. The percentage of saturation indicated in this table is the sum of C12:0, C14:0, and C16:0 fatty alcohols. However, the strain with the Pho17-fabA construction produced 25% less fatty alcohols and these fatty alcohols had a higher saturation level. These results indicate that the total capacity to produce fatty acids, as well as the unsaturated fatty acid production level were lower in this strain. Both of these phenotypes would be expected for a lower level of fabA expression, indicating that Pho17 is a weaker promoter than either Pho1 or the native promoter.

TABLE 14-1

| Fatty Alcohol Production | | |
|---|---|---|
| Strain | Total Fatty Alcohols (g/L) | Percentage of Saturation of the Fatty Alcohols |
| W3110K-Δ4/pCDX11-8087 | ~3 | 53% |
| W3110K-Δ4::Km-Pho1-fabA/pCDX11-8087 | ~3 | 56% |
| W3110K-Δ4::KmPho17-fabA/pCDX11-8087 | ~2 | 73% |

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some embodiments and optional features, modification and variation of the concepts herein disclosed may be utilized by those skilled in the art, and that such modifications and variations are considered to be within the scope of the present invention.

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed is:

1. A low-phosphate repressible promoter comprising Pho1, wherein said low-phosphate repressible promoter comprises SEQ ID NO: 4.

2. An expression construct comprising at least one low-phosphate repressible promoter provided in claim 1.

3. A recombinant host cell comprising at least one low-phosphate repressible promoter, wherein said promoter is the low-phosphate repressible promoter set forth in claim 1.

4. The recombinant host cell of claim 3, wherein said recombinant host cell is *E. coli*.

5. The recombinant host cell of claim 3, wherein said recombinant host cell is present within a culture medium.

6. The recombinant host cell of claim 3, wherein at least one gene is under the control of the at least one low-phosphate repressible promoter.

7. The recombinant host cell of claim 3, wherein said recombinant host cell is present within a culture medium and the expression of at least one gene is under the control of the at least one low-phosphate repressible promoter which responds to the phosphate concentration of said culture medium.

* * * * *

SEQUENCE LISTING

<160> NUMBER OF SEQ ID NOS: 63

<210> SEQ ID NO 1
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 1
ctktcatawa wctgtcay                                                        18

<210> SEQ ID NO 2
<211> LENGTH: 346
<212> TYPE: PRT
<213> ORGANISM: Escherichia coli

<400> SEQUENCE: 2

Met Lys Val Met Arg Thr Thr Val Ala Thr Val Ala Ala Thr Leu
1               5                   10                  15

Ser Met Ser Ala Phe Ser Val Phe Ala Glu Ala Ser Leu Thr Gly Ala
            20                  25                  30

Gly Ala Thr Phe Pro Ala Pro Val Tyr Ala Lys Trp Ala Asp Thr Tyr
        35                  40                  45

Gln Lys Glu Thr Gly Asn Lys Val Asn Tyr Gln Gly Ile Gly Ser Ser
    50                  55                  60

Gly Gly Val Lys Gln Ile Ile Ala Asn Thr Val Asp Phe Gly Ala Ser
65                  70                  75                  80

Asp Ala Pro Leu Ser Asp Glu Lys Leu Ala Gln Glu Gly Leu Phe Gln
                85                  90                  95

Phe Pro Thr Val Ile Gly Gly Val Val Leu Ala Val Asn Ile Pro Gly
            100                 105                 110

Leu Lys Ser Gly Glu Leu Val Leu Asp Gly Lys Thr Leu Gly Asp Ile
        115                 120                 125

Tyr Leu Gly Lys Ile Lys Lys Trp Asp Asp Glu Ala Ile Ala Lys Leu
    130                 135                 140

Asn Pro Gly Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Glu Trp Lys Asn Asn Val Gly Thr Gly Ser Thr Val Lys
            180                 185                 190

Trp Pro Ile Gly Leu Gly Gly Lys Gly Asn Asp Gly Ile Ala Ala Phe
        195                 200                 205

Val Gln Arg Leu Pro Gly Ala Ile Gly Tyr Val Glu Tyr Ala Tyr Ala
    210                 215                 220

Lys Gln Asn Asn Leu Ala Tyr Thr Lys Leu Ile Ser Ala Asp Gly Lys
225                 230                 235                 240

Pro Val Ser Pro Thr Glu Glu Asn Phe Ala Asn Ala Ala Lys Gly Ala
                245                 250                 255

Asp Trp Ser Lys Thr Phe Ala Gln Asp Leu Thr Asn Gln Lys Gly Glu
            260                 265                 270

Asp Ala Trp Pro Ile Thr Ser Thr Phe Ile Leu Ile His Lys Asp
        275                 280                 285

Gln Lys Lys Pro Glu Gln Gly Thr Glu Val Leu Lys Phe Phe Asp Trp
    290                 295                 300

Ala Tyr Lys Thr Gly Ala Lys Gln Ala Asn Asp Leu Asp Tyr Ala Ser
305                 310                 315                 320

Leu Pro Asp Ser Val Val Glu Gln Val Arg Ala Ala Trp Lys Thr Asn
            325                 330                 335

Ile Lys Asp Ser Ser Gly Lys Pro Leu Tyr
            340                 345

<210> SEQ ID NO 3
<211> LENGTH: 1041
<212> TYPE: DNA
<213> ORGANISM: Escherichia coli

<400> SEQUENCE: 3

| | | | | | | |
|---|---|---|---|---|---|---|
| atgaaagtta | tgcgtaccac | cgtcgcaact | gttgtcgccg | cgaccttatc | gatgagtgct | 60 |
| ttctctgtgt | ttgcagaagc | aagcctgaca | ggtgcaggtg | caaccttccc | tgcgccggtg | 120 |
| tatgccaaat | gggctgacac | ttaccagaaa | gaaaccggta | taaagttaa | ctaccagggt | 180 |
| atcggttctt | ccggtggcgt | aaaacagatt | atcgctaata | ccgttgattt | tggtgcctct | 240 |
| gacgcgccgc | tgtctgacga | aaaactggct | caggaaggtc | tgttccagtt | cccgaccgtg | 300 |
| attggcggcg | tggtgctggc | ggttaacatt | ccagggctga | agtctggcga | actggtgctg | 360 |
| gatggtaaaa | ccctcggcga | catctacctg | ggcaaaatca | agaagtggga | tgatgaagcc | 420 |
| atcgccaaac | tgaatccggg | tctgaaactg | ccttcacaaa | acattgctgt | agtacgccgc | 480 |
| gcagatggct | ccgggacttc | cttcgtcttc | accagctacc | tggcgaaagt | gaacgaagag | 540 |
| tggaaaaaca | acgttggtac | tggctctacc | gtaaaatggc | cgatcggtct | gggcggtaaa | 600 |
| ggtaacgacg | gtatcgccgc | gttcgttcag | cgtctgccgg | gtgcaattgg | ttatgttgaa | 660 |
| tatgcttacg | cgaagcagaa | caacctggcg | tacaccaaac | tgatctccgc | tgatggtaaa | 720 |
| ccggttagtc | cgaccgaaga | aaacttcgct | aatgcagcaa | aggtgcaga | ctggagcaaa | 780 |
| accttcgctc | aggatctgac | caaccagaaa | ggcgaagatg | catggcctat | acctctacc | 840 |
| acgttcattc | tgatccacaa | agatcagaag | aaaccagaac | aaggcacaga | agtgctgaaa | 900 |
| ttcttcgact | gggcgtacaa | accggggct | aaacaggcga | acgacctgga | ttacgccagc | 960 |
| ctgccggata | gtgtagttga | acaggttcgc | gctgcgtgga | agaccaatat | aaagacagt | 1020 |
| agcggtaagc | cgctgtacta | a | | | | 1041 |

<210> SEQ ID NO 4
<211> LENGTH: 818
<212> TYPE: DNA
<213> ORGANISM: Artificial Sequence
<220> FEATURE:
<223> OTHER INFORMATION: Synthetic polynucleotide

<400> SEQUENCE: 4

| | | | | | | |
|---|---|---|---|---|---|---|
| ccagcgtgga | ccgcttgctg | caactctctc | agggccaggc | ggtgaagggc | aatcagctgt | 60 |
| tgcccgtctc | actggtgaaa | agaaaaacca | ccctggcgcc | caatacgcaa | accgcctctc | 120 |
| cccgcgcgtt | ggccgattca | ttaatgcagc | tggcacgaca | ggtttcccga | ctggaaagcg | 180 |
| ggcagtaata | aaaatgccag | ccgatcgggc | tggcattttt | gcctttaaat | tggtttgaca | 240 |
| gcttatcatc | gactgcacgg | tgcaccaatg | cttctggcgt | caggcagcca | tcggaagctg | 300 |
| tggtatggct | gtgcaggtcg | taaatcactg | cataattcgt | gtcgctcaag | gcgcactccc | 360 |
| gttctggata | atgttttttg | cgccgacatg | tttgtgacag | atatatgaca | ggaatttgac | 420 |
| agatatatga | caggctggta | taatgcgcca | ccactgacac | ggaacaacgg | cgcgccgctg | 480 |

```
agaaaaagcg aagcggcact gctctttaac aatttatcag acaatctgtg tgggcactcg      540
accggaatta tcgattaact ttattattaa aaattaaaga ggtatatatt aatgtatcga      600
ttaaataagg aggaataaac catgaccatg attacggatt cactggccgt cgttttacaa      660
cgtcgtgact gggaaaaccc tggcgttacc caacttaatc gccttgcagc acatcccccct     720 ttcgccagct ggcgtaatag cgaagaggcc cgcaccgatc gcccttccca acagttgcgc      780
agcctgaatg gcgaatggcg ctttgcctgg tttccggc                              818
```

<210> SEQ ID NO 5
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 5

```
gtgacagata tatgacagga atgtgacaga tatatgacag gctggtataa tgcgccacca       60
```

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 9

```
agtataggaa cttcgaagca gctccagcct acaaataaaa atgccagccg atcgggctgg       60
```

<210> SEQ ID NO 10
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 10

```
tcattcaata cctctgtaag tcgcacatag agtaagtttc tggtggcgca ttataccagc       60
```

<210> SEQ ID NO 11
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 11

```
aggcggtggc tcgatcttag cgatgtgtgt aaggctgcgc attccgggga tccgtcgacc        60
```

<210> SEQ ID NO 12
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 12

```
aaaggcaaaa atgccagccc gatcggctgg catttttatt tgtaggctgg agctgcttcg        60
```

<210> SEQ ID NO 13
<211> LENGTH: 1641
<212> TYPE: DNA
<213> ORGANISM: Artificial Sequence
<220> FEATURE:
<223> OTHER INFORMATION: Synthetic polynucleotide

<400> SEQUENCE: 13

```
aggcggtggc tcgatcttag cgatgtgtgt aaggctgcgc attccgggga tccgtcgacc        60
tgcagttcga agttcctatt ctctagaaag tataggaact tcagagcgct tttgaagctc       120
acgctgccgc aagcactcag ggcgcaaggg ctgctaaagg aagcggaaca cgtagaaagc       180
cagtccgcag aaacggtgct gaccccggat gaatgtcagc tactgggcta tctggacaag       240
ggaaaacgca agcgcaaaga gaaagcaggt agcttgcagt gggcttacat ggcgatagct       300
agactgggcg gttttatgga cagcaagcga accggaattg ccagctgggg cgccctctgg       360
taaggttggg aagccctgca agtaaactg atggctttc ttgccgccaa ggatctgatg       420
gcgcagggga tcaagatctg atcaagagac aggatgagga tcgtttcgca tgattgaaca       480
agatggattg cacgcaggtt ctccggccgc ttgggtggag aggctattcg gctatgactg       540
ggcacaacag acaatcggct gctctgatgc cgccgtgttc cggctgtcag cgcaggggcg       600
cccggttctt tttgtcaaga ccgacctgtc cggtgccctg aatgaactgc aggacgaggc       660
agcgcggcta tcgtggctgg ccacgacggg cgttccttgc gcagctgtgc tcgacgttgt       720
cactgaagcg ggaagggact ggctgctatt gggcgaagtg ccggggcagg atctcctgtc       780
atctcacctt gctcctgccg agaaagtatc catcatggct gatgcaatgc ggcggctgca       840
tacgcttgat ccggctacct gcccattcga ccaccaagcg aaacatcgca tcgagcgagc       900
acgtactcgg atggaagccg gtcttgtcga tcaggatgat ctggacgaag agcatcaggg       960
gctcgcgcca gccgaactgt tcgccaggct caaggcgcgc atgcccgacg gcgaggatct      1020
cgtcgtgacc catggcgatg cctgcttgcc gaatatcatg gtggaaaatg gccgcttttc      1080
tggattcatc gactgtggcc ggctgggtgt ggcggaccgc tatcaggaca tagcgttggc      1140
tacccgtgat attgctgaag agcttggcgg cgaatgggct gaccgcttcc tcgtgcttta      1200
cggtatcgcc gctcccgatt cgcagcgcat cgccttctat cgccttcttg acagttctt       1260 ctaataaggg gatcttgaag ttcctattcc gaagttccta ttctctagaa agtataggaa      1320
cttcgaagca gctccagcct acaaataaaa atgccagccg atcgggctgg catttttgcc      1380
tttaaattgg tttgacagct tatcatcgac tgcacggtgc accaatgctt ctggcgtcag      1440
gcagccatcg gaagctgtgg tatggctgtg caggtcgtaa atcactgcat aattcgtgtc      1500
gctcaaggcg cactcccgtt ctggataatg ttttttgcgc cgacatgttt gtgacagata      1560
tatgacagga atttgacaga tatatgcag gctggtataa tgcgccacca gaaacttact      1620
ctatgtgcga cttacagagg t                                                1641
```

<210> SEQ ID NO 14
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 14
ttggaaaaat agacatcgtc aaaatctc                                        28

<210> SEQ ID NO 15
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 15
tgcagcgcaa ggcgaggagt atccccgtct                                      30

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
attccgggga tccgtcgacc                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
ggcacaacag acaatcggct                                                 20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
cctgcttgcc gaatatcatg                                                 20

<210> SEQ ID NO 19
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 19
gcctttaaat tggtttgaca gct                                             23

<210> SEQ ID NO 20
<211> LENGTH: 21
<212> TYPE: DNA
<213> ORGANISM: Artificial Sequence
<220> FEATURE:

<223> OTHER INFORMATION: Synthetic polynucleotide

<400> SEQUENCE: 20
cgtgcagtga ttactggcct g                                     21

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
atgtggtcac caaagcgatg                                       20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
ggtacttcga ctccggttgg                                       20

<210> SEQ ID NO 23
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 23
ctggtaatgc gcaagctgaa                                       20

<210> SEQ ID NO 24
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 24
aatgcccagg ccagtaatc                                        19

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
tatctgtcac aaacatgtcg                                       20

<210> SEQ ID NO 26
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 26
tctgacgcat atcgacgcag aagt                                  24

```
<210> SEQ ID NO 27
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 27
gccgctccag aatctcaaag caat                                              24

<210> SEQ ID NO 28
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 28
ttgtcggcgg tggtgatgtc a                                                 21

<210> SEQ ID NO 29
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 29
atgcggtgaa ctgtggaata a                                                 21

<210> SEQ ID NO 30
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 30
atctctgcgt gaaggacgcg tt                                                22

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
atgaggccag tggtatccag                                                   20

<210> SEQ ID NO 32
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 32

His Leu Val Asp Glu Pro Gln Asn Leu Ile Lys
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic polypeptide
```

```
<400> SEQUENCE: 33

Leu Gly Glu Tyr Gly Phe Gln Asn Ala Leu Ile Val Arg
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 34

Leu Phe Thr Phe His Ala Asp Ile Cys Thr Leu Pro Asp Thr Glu Lys
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 35

Arg Pro Cys Phe Ser Ala Leu Thr Pro Asp Glu Thr Tyr Val Pro Lys
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 36

Val Gly Leu Ile Ala Gly Ser Gly Gly Gly Ser Pro Arg
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 37

Leu Asp Thr Thr Gly Leu Ile Asp Arg
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 38

Ala Val Gly Pro Tyr Val Val Thr Lys
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic polypeptide
```

<400> SEQUENCE: 39

Ser Gly Ile Thr Phe Ser Gln Glu Leu Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 40

Phe Gln Val Phe Gly Ala Asp Ala Met Arg
1               5                   10

<210> SEQ ID NO 41
<211> LENGTH: 7332
<212> TYPE: DNA
<213> ORGANISM: Artificial Sequence
<220> FEATURE:
<223> OTHER INFORMATION: Synthetic polynucleotide

<400> SEQUENCE: 41

| | | | | | | |
|---|---|---|---|---|---|---|
| ggcatccgct | tacagacaag | ctgtgaccgt | ctccgggagc | tgcatgtgtc | agaggttttc | 60 |
| accgtcatca | ccgaaacgcg | cgaggcagca | gatcaattcg | cgcgcgaagg | cgaagcggca | 120 |
| tgcatttacg | ttgacaccat | cgaatggtgc | aaaacctttc | gcggtatggc | atgatagcgc | 180 |
| ccggaagaga | gtcaattcag | ggtggtgaat | gtgaaaccag | taacgttata | cgatgtcgca | 240 |
| gagtatgccg | gtgtctctta | tcagaccgtt | tcccgcgtgg | tgaaccaggc | cagccacgtt | 300 |
| tctgcgaaaa | cgcgggaaaa | agtggaagcg | gcgatggcgg | agctgaatta | cattcccaac | 360 |
| cgcgtggcac | aacaactggc | gggcaaacag | tcgttgctga | ttggcgttgc | cacctccagt | 420 |
| ctggccctgc | acgcgccgtc | gcaaattgtc | gcggcgatta | aatctcgcgc | cgatcaactg | 480 |
| ggtgccagcg | tggtggtgtc | gatggtagaa | cgaagcggcg | tcgaagcctg | taaagcggcg | 540 |
| gtgcacaatc | ttctcgcgca | acgcgtcagt | gggctgatca | ttaactatcc | gctggatgac | 600 |
| caggatgcca | ttgctgtgga | agctgcctgc | actaatgttc | cggcgttatt | cttgatgtc | 660 |
| tctgaccaga | cacccatcaa | cagtattatt | ttctcccatg | aagacggtac | gcgactgggc | 720 |
| gtggagcatc | tggtcgcatt | gggtcaccag | caaatcgcgc | tgttagcggg | cccattaagt | 780 |
| tctgtctcgg | cgcgtctgcg | tctggctggc | tggcataaat | atctcactcg | caatcaaatt | 840 |
| cagccgatag | cggaacggga | aggcgactgg | agtgccatgt | ccggttttca | acaaaccatg | 900 |
| caaatgctga | atgagggcat | cgttcccact | gcgatgctgg | ttgccaacga | tcagatggcg | 960 |
| ctgggcgcaa | tgcgcgccat | taccgagtcc | gggctgcgcg | ttggtgcgga | tatctcggta | 1020 |
| gtgggatacg | acgataccga | agacagctca | tgttatatcc | cgccgttaac | caccatcaaa | 1080 |
| caggattttc | gcctgctggg | gcaaaccagc | gtggaccgct | tgctgcaact | ctctcagggc | 1140 |
| caggcggtga | agggcaatca | gctgttgccc | gtctcactgg | tgaaaagaaa | aaccaccctg | 1200 |
| gcgcccaata | cgcaaaccgc | ctctccccgc | gcgttggccg | attcattaat | gcagctggca | 1260 |
| cgacaggttt | cccgactgga | aagcgggcag | taataattta | aattggtttg | acagcttatc | 1320 |
| atcgactgca | cggtgcacca | atgcttctgg | cgtcaggcag | ccatcggaag | ctgtggtatg | 1380 |
| gctgtgcagg | tcgtaaatca | ctgcataatt | cgtgtcgctc | aaggcgcact | cccgttctgg | 1440 |
| ataatgtttt | ttgcgccgac | ataattgtga | gcgctcacaa | tttctgaaat | gagctgttga | 1500 |
| caattaatca | tccggctcgt | ataatgtgtg | gaattgtgag | cggataacaa | tttcacacag | 1560 |

```
gaaacagcgc cgctgagaaa aagcgaagcg gcactgctct ttaacaattt atcagacaat    1620
ctgtgtgggc actcgaccgg aattatcgat taactttatt attaaaaatt aaaggaggaa    1680
taaaccatgg cgactcaaca acagaacaac ggtgcatctg catccggcgt cttggaaatt    1740
cttcgtggaa agcacgttct tatcacaggt actaccggat ttttgggcaa agtggttctg    1800
gaaaagttga ttcgtactgt tccggatatt ggaggtattc atctgctgat tcgtggcaat    1860
aaacgtcatc cagccgctcg cgaacgtttc ctgaacgaaa ttgcgtcctc ctccgtcttc    1920
gaacgtttgc gtcacgatga taatgaagcc ttcgagacct tcttggaaga acgtgttcac    1980
tgtattaccg gtgagattac tgaatcccgt tttggtttga cacctgagcg ttttcgtgct    2040
ttggccggtc aggttgacgc ttttattcat agcgctgcaa gcgtgaactt cgtgagcaa    2100 ttggataaag ccctgaaaat caacaccttg tgtcttgaaa atgttgctgc tcttgcagaa    2160
ttgaactccg ctatggcggt cattcaggtt tccacttgtt acgttaacgg taaaacctcc    2220
ggtcaaatta ccgaatccgt cattaaatcg gctggcgaat ccattccccg ttccactgac    2280
ggttactacg agatcgaaga attggtccat ctgttgcaag acaagatttc cgatgttaaa    2340
gctcgttact ccgccgtgt tatggggaaa aaattggttg atttgggtat tcgtgaggcc    2400
aataattacg gatggtccga cacctacaca ttcaccaaat ggttgggtga acaactgctg    2460
atgaaggcct tgtctggtcg ttctttgact attgtgcgtc cctctattat tgagtccgct    2520
ttggaagaac cttcccctgg ttggatcgaa ggcgttaaag ttgccgatgc cattatcttg    2580
gcttatgccc gtgaaaaagt tagcctgttc cctggaaaac gttccggcat tattgatgtt    2640
attcctgtcg atttggttgc gaactccatc atcttgtctc tggctgaggc gttgtctggt    2700
tctggtcaac gtcgtatta tcaatgttgc agcggtggtt ctaatccaat ctcccctgggt    2760 aagttcattg attatttgaa cgccgaggct aagaccaact atgctgccta cgatcaactg    2820 tttatcgtc gtcctactaa accttttcgt gccgtgaacc gtaaattgtt tgacgttgtt    2880
gttggtgtca tgcgtgttgt cctttctatt gcccgcaaag ctatgcgttt ggctggtgta    2940
aatcgtgagt tgaaagtgct taagaacctt gatacgaccc gtaaacttgc aaccattttt    3000
ggcttctata ctgctcccga ctatatcttc cgtaacgata gcttgatggc cctggctcag    3060
cgtatgggtg aattggatcg tgttctttc ccagttgatg ctcgtcaaat tgattggcag    3120
ttgtacttgt gtaaaattca tttgcgtggt ctgaaccgtt acgctttgaa ggaacgtaaa    3180
ctgtattctt cgcgtgctgc tgatactgac gataaaaccg cctaagtcga catagatcta    3240
gaacttactc ggaagcttct taattaagag gatccattga cgtctatgaa ttcgtttaaa    3300
cggtctccag cttggctgtt ttggcggatg agagaagatt ttcagcctga tacagattaa    3360
atcagaacga gaagcggtc tgataaaaca gaatttgcct ggcggcagta gcgcggtggt    3420
cccacctgac cccatgccga actcagaagt gaaacgccgt agcgccgatg gtagtgtggg    3480
gtctccccat gcgagagtag ggaactgcca ggcatcaaat aaaacgaaag gctcagtcga    3540
aagactgggc cttcgtttt atctgttgtt tgtcggtgaa cgctctcctg aggcgcctga    3600
tgcggtattt tctccttacg catctgtgcg gtatttcaca ccgcatatgg tgcactctca    3660
gtacaatctg ctctgatgcc gcatagttaa gccagccccg acacccgcca cacccgctg    3720 acgagcttag taaagccctc gctagatttt aatgcggatg ttgcgattac ttcgccaact    3780
attgcgataa caagaaaaag ccagcctttt atgatatatc tcccaatttg tgtagggctt    3840
attatgcacg cttaaaaata taaaagcag acttgacctg atagtttggc tgtgagcaat    3900
```

```
tatgtgctta gtgcatctaa cgcttgagtt aagccgcgcc gcgaagcggc gtcggcttga    3960
acgaattgtt agacattatt tgccgactac cttggtgatc tcgcctttca cgtagtggac    4020
aaattcttcc aactgatctg cgcgcgaggc caagcgatct tcttcttgtc caagataagc    4080
ctgtctagct tcaagtatga cgggctgata ctgggccggc aggcgctcca ttgcccagtc    4140
ggcagcgaca tccttcggcg cgattttgcc ggttactgcg ctgtaccaaa tgcgggacaa    4200
cgtaagcact acatttcgct catcgccagc ccagtcgggc ggcgagttcc atagcgttaa    4260
ggtttcattt agcgcctcaa atagatcctg ttcaggaacc ggatcaaaga gttcctccgc    4320
cgctggacct accaaggcaa cgctatgttc tcttgctttt gtcagcaaga tagccagatc    4380
aatgtcgatc gtggctggct cgaagatacc tgcaagaatg tcattgcgct gccattctcc    4440
aaattgcagt tcgcgcttag ctggataacg ccacggaatg atgtcgtcgt gcacaacaat    4500
ggtgacttct acagcgcgga gaatctcgct ctctccaggg gaagccgaag tttccaaaag    4560
gtcgttgatc aaagctcgcc gcgttgtttc atcaagcctt acggtcaccg taaccagcaa    4620
atcaatatca ctgtgtggct tcaggccgcc atccactgcg gagccgtaca aatgtacggc    4680
cagcaacgtc ggttcgagat ggcgctcgat gacgccaact acctctgata gttgagtcga    4740
tacttcggcg atcaccgctt ccctcatgat gtttaacttt gttttagggc gactgccctg    4800
ctgcgtaaca tcgttgctgc tccataacat caaacatcga cccacggcgt aacgcgcttg    4860
ctgcttggat gcccgaggca tagactgtac cccaaaaaaa cagtcataac aagccatgaa    4920
aaccgccact gcgccgttac caccgctgcg ttcggtcaag gttctggacc agttgcgtga    4980
gcgcatacgc tacttgcatt acagcttacg aaccgaacag gcttatgtcc actgggttcg    5040
tgccttcatc cgtttccacg gtgtgcgtca cccggcaacc ttgggcagca gcgaagtcga    5100
ggcatttctg tcctgctggc gaacgagcg caaggtttcg gtctccacgc atcgtcaggc    5160
attggcggcc ttgctgttct tctacggcaa ggtgctgtgc acggatctgc cctggcttca    5220
ggagatcgga agacctcggc cgtcgcgcg cttgccggtg gtgctgaccc cggatgaagt    5280
ggttcgcatc ctcggttttc tggaaggcga gcatcgtttg ttcgcccagc ttctgtatgg    5340
aacgggcatg cggatcagtg agggtttgca actgcgggtc aaggatctgg atttcgatca    5400
cggcacgatc atcgtgcggg agggcaaggg ctccaaggat cgggccttga tgttacccga    5460
gagcttggca cccagcctgc gcgagcaggg gaattaattc ccacgggttt gctgcccgc    5520 aaacgggctg ttctggtgtt gctagttttgt tatcagaatc gcagatccgg cttcagccgg    5580
tttgccggct gaaagcgcta tttcttccag aattgccatg atttttttccc cacgggaggc    5640 gtcactggct cccgtgttgt cggcagcttt gattcgataa gcagcatcgc ctgtttcagg    5700
ctgtctatgt gtgactgttg agctgtaaca agttgtctca ggtgttcaat tcatgttct    5760 agttgctttg ttttactggt ttcacctgtt ctattaggtg ttacatgctg ttcatctgtt    5820
acattgtcga tctgttcatg gtgaacagct tgaatgcac caaaaactcg taaaagctct    5880
gatgtatcta tcttttttac accgttttca tctgtgcata tggacagttt tcccttttgat    5940 atgtaacggt gaacagttgt tctactttttg tttgttagtc ttgatgcttc actgatagat    6000
acaagagcca taagaacctc agatccttcc gtatttagcc agtatgttct ctagtgtggt    6060
tcgttgtttt tgcgtgagcc atgagaacga accattgaga tcatacttac tttgcatgtc    6120
actcaaaaat tttgcctcaa aactggtgag ctgaattttt gcagttaaag catcgtgtag    6180 tgttttttctt agtccgttat gtaggtagga atctgatgta atggttgttg gtattttgtc    6240
accattcatt tttatctggt tgttctcaag ttcggttacg agatccattt gtctatctag    6300
```

```
ttcaacttgg aaaatcaacg tatcagtcgg gcggcctcgc ttatcaacca ccaatttcat    6360
attgctgtaa gtgtttaaat ctttacttat tggtttcaaa acccattggt taagccttt     6420 aaactcatgg tagttatttt caagcattaa catgaactta aattcatcaa ggctaatctc    6480
tatatttgcc ttgtgagttt tcttttgtgt tagttctttt aataaccact cataaatcct    6540
catagagtat ttgttttcaa aagacttaac atgttccaga ttatatttta tgaattttt    6600 taactggaaa agataaggca atatctcttc actaaaaact aattctaatt tttcgcttga    6660
gaacttggca tagtttgtcc actggaaaat ctcaaagcct ttaaccaaag gattcctgat    6720
ttccacagtt ctcgtcatca gctctctggt tgctttagct aatacaccat aagcattttc    6780
cctactgatg ttcatcatct gagcgtattg gttataagtg aacgataccg tccgttcttt    6840
ccttgtaggg ttttcaatcg tggggttgag tagtgccaca cagcataaaa ttagcttggt    6900
ttcatgctcc gttaagtcat agcgactaat cgctagttca tttgctttga aaacaactaa    6960
ttcagacata catctcaatt ggtctaggtg attttaatca ctataccaat tgagatgggc    7020
tagtcaatga taattactag tccttttcct ttgagttgtg ggtatctgta aattctgcta    7080
gacctttgct ggaaaacttg taaattctgc tagaccctct gtaaattccg ctagaccttt    7140
gtgtgttttt tttgtttata ttcaagtggt tataatttat agaataaaga aagaataaaa    7200
aaagataaaa agaatagatc ccagcccctgt gtataactca ctactttagt cagttccgca   7260
gtattacaaa aggatgtcgc aaacgctgtt tgctcctcta caaaacagac cttaaaaccc    7320
taaaggctta ag                                                        7332

<210> SEQ ID NO 42
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 42
ctgtcagccg ttaagtgttc ctgtg                                           25

<210> SEQ ID NO 43
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 43
cagttcaacc tgttgatagt acg                                             23

<210> SEQ ID NO 44
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 44
atatgacagg aatgtgacag a                                               21

<210> SEQ ID NO 45
<211> LENGTH: 1641
<212> TYPE: DNA
<213> ORGANISM: Artificial Sequence
<220> FEATURE:
```

<223> OTHER INFORMATION: Synthetic polynucleotide

<400> SEQUENCE: 45

```
aggcggtggc tcgatcttag cgatgtgtgt aaggctgcgc attccgggga tccgtcgacc      60
tgcagttcga agttcctatt ctctagaaag tataggaact tcagagcgct tttgaagctc     120
acgctgccgc aagcactcag ggcgcaaggg ctgctaaagg aagcggaaca cgtagaaagc     180
cagtccgcag aaacggtgct gaccccggat gaatgtcagc tactgggcta tctggacaag     240
ggaaaacgca agcgcaaaga gaaagcaggt agcttgcagt gggcttacat ggcgatagct     300
agactgggcg gttttatgga cagcaagcga accggaattg ccagctgggg cgccctctgg     360
taaggttggg aagccctgca agtaaactg gatggctttc ttgccgccaa ggatctgatg      420
gcgcagggga tcaagatctg atcaagagac aggatgagga tcgtttcgca tgattgaaca     480
agatggattg cacgcaggtt ctccggccgc ttgggtggag aggctattcg gctatgactg     540
ggcacaacag acaatcggct gctctgatcg cgcgtgttc cggctgtcag cgcaggggcg      600
cccggttctt tttgtcaaga ccgacctgtc cggtgccctg aatgaactgc aggacgaggc     660
agcgcggcta tcgtggctgg ccacgacggg cgttccttgc gcagctgtgc tcgacgttgt     720
cactgaagcg ggaagggact ggctgctatt gggcgaagtg ccggggcagg atctcctgtc     780
atctcacctt gctcctgccg agaaagtatc catcatggct gatgcaatgc ggcggctgca     840
tacgcttgat ccggctacct gcccattcga ccaccaagcg aaacatcgca tcgagcgagc     900
acgtactcgg atggaagccg gtcttgtcga tcaggatgat ctggacgaag agcatcaggg     960
gctcgcgcca gccgaactgt tcgccaggct caaggcgcgc atgcccgacg gcgaggatct    1020
cgtcgtgacc catggcgatg cctgcttgcc gaatatcatg gtggaaaatg gccgcttttc    1080
tggattcatc gactgtggcc ggctgggtgt ggcggaccgc tatcaggaca tagcgttggc    1140
tacccgtgat attgctgaag agcttggcgg cgaatgggct gaccgcttcc tcgtgcttta    1200
cggtatcgcc gctcccgatt cgcagcgcat cgccttctat cgccttcttg acgagttctt    1260
ctaataaggg gatcttgaag ttcctattcc gaagttccta ttctctagaa agtataggaa    1320
cttcgaagca gctccagcct acaaataaaa atgccagccg atcgggctgg cattttttgcc   1380
tttaaattgg tttgacagct tatcatcgac tgcacggtgc accaatgctt ctggcgtcag    1440
gcagccatcg gaagctgtgg tatggctgtg caggtcgtaa atcactgcat aattcgtgtc    1500
gctcaaggcg cactcccgtt ctggataatg ttttttgcgc cgacatgttt gtgacagata    1560
tatgacagga atgtgacaga tatatgcacg gctggtataa tgcgccacca gaaacttact    1620
ctatgtgcga cttacagagg t                                                1641
```

<210> SEQ ID NO 46
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 46

```
acgttatcat tcactttaca tcagagatat accaatggcg attccgggga tccgtcgacc      60
```

<210> SEQ ID NO 47
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 47
agagaaatta gaaacggaag gttgcggttg caacgacctg tgtaggctgg agctgcttcg    60

<210> SEQ ID NO 48
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: 5' tetranucleotide modified with
      phosphorothioate bonds.

<400> SEQUENCE: 48
agagaaatta gaaacggaag gttgcggttg caacgacctg cgccattggt atatctctga    60
tgtaaagtga atgataacgt                                                80

<210> SEQ ID NO 49
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 49
agcttaaatg tgattcaaca tcactggaga aagtcttatg attccgggga tccgtcgacc    60

<210> SEQ ID NO 50
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 50
atgcagggga gcggcaagat taaaccagtt cgttcgggca tgtaggctgg agctgcttcg    60

<210> SEQ ID NO 51
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: 5' tetranucleotide modified with
      phosphorothioate bonds.

<400> SEQUENCE: 51
agcttaaatg tgattcaaca tcactggaga aagtcttatg tgcccgaacg aactggttta    60
atcttgccgc tcccctgcat                                                80

<210> SEQ ID NO 52
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 52
atttactaaa aaagtttaac attatcagga gagcattatg attccgggga tccgtcgacc    60

```
<210> SEQ ID NO 53
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 53
tgccagacag cgctactgat taagcggatt ttttcgcttt tgtaggctgg agctgcttcg    60

<210> SEQ ID NO 54
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: 5' tetranucleotide modified with
      phosphorothioate bonds.

<400> SEQUENCE: 54
atttactaaa aaagtttaac attatcagga gagcattatg aaagcgaaaa aatccgctta    60
atcagtagcg ctgtctggca                                               80

<210> SEQ ID NO 55
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 55
aggataatta ctctgccaaa gtgataaata acaatgatg attccgggga tccgtcgacc    60

<210> SEQ ID NO 56
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 56
gcaatctaaa gttaatcttc tccacattaa caatatggtg tgtaggctgg agctgcttcg    60

<210> SEQ ID NO 57
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: 5' tetranucleotide modified with
      phosphorothioate bonds.

<400> SEQUENCE: 57
gcaatctaaa gttaatcttc tccacattaa caatatggtg catcattgtt tatttatcac    60
tttggcagag taattatcct                                               80

<210> SEQ ID NO 58
<211> LENGTH: 60
<212> TYPE: DNA
<213> ORGANISM: Artificial Sequence
```

```
<220> FEATURE:
<223> OTHER INFORMATION: Synthetic polynucleotide

<400> SEQUENCE: 58
ggccattacg ttggctgaac tggtttattc cgaactgatc attccgggga tccgtcgacc    60

<210> SEQ ID NO 59
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 59
gtttatctac catgttctct gtaagcctta ttttattgaa gtggtggcgc attataccag    60
c                                                                   61

<210> SEQ ID NO 60
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 60
tggcgaaggc caaacgacgc                                                20

<210> SEQ ID NO 61
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 61
tcatcagcat gttcggtgct ggc                                            23

<210> SEQ ID NO 62
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 62
tggtggcgca ttataccagc ctgtcatata tctgtcaaat tcctgtcata tatctgtcac    60

<210> SEQ ID NO 63
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 63
tggtggcgca ttataccagc ctgtcatata tctgtcacat tcctgtcata tatctgtcac    60
```